United States Patent

Matsumura et al.

[11] Patent Number: 5,616,732
[45] Date of Patent: Apr. 1, 1997

[54] INTERMEDIATES FOR DIFLUOROPROSTACYCLINS AND METHODS FOR THEIR PRODUCTION

[75] Inventors: Yasushi Matsumura; Takashi Nakano; Mayumi Makino; Yoshitomi Morizawa, all of Yokohama, Japan

[73] Assignee: Asahi Glass Company Ltd., Tokyo, Japan

[21] Appl. No.: 600,824

[22] Filed: Feb. 13, 1996

Related U.S. Application Data

[62] Division of Ser. No. 390,316, Feb. 17, 1995, Pat. No. 5,538,995.

[30] Foreign Application Priority Data

| Feb. 17, 1994 | [JP] | Japan | 6-20450 |
| Mar. 17, 1994 | [JP] | Japan | 6-46853 |
| Apr. 8, 1994 | [JP] | Japan | 6-71097 |
| Apr. 11, 1994 | [JP] | Japan | 6-71989 |
| Apr. 19, 1994 | [JP] | Japan | 6-80641 |
| Nov. 17, 1994 | [JP] | Japan | 6-283857 |

[51] Int. Cl.⁶ .................. C07D 307/935; C07D 307/937
[52] U.S. Cl. .......................... 549/305; 549/465
[58] Field of Search ........................ 549/465, 305

[56] References Cited

PUBLICATIONS

Umemoto et al., J.A.C.S., vol. 112, pp. 8563–8575 (1990).

*Primary Examiner*—Bernard Dentz
*Attorney, Agent, or Firm*—Oblon, Spivak, McClelland, Maier & Neustadt, P.C.

[57] ABSTRACT

A difluoroprostacyclin of the following formula (V), its lower alkanol ester or its pharmaceutically acceptable salt:

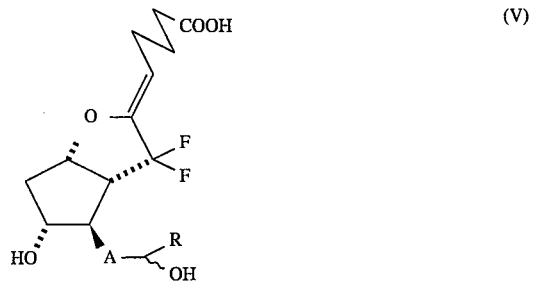

wherein A is an ethylene group, a vinylene group or an ethynylene group, R is a substituted or unsubstituted $C_{1-10}$ alkyl group, a substituted or unsubstituted $C_{1-10}$ alkenyl group, a substituted or unsubstituted $C_{1-10}$ alkynyl group, a substituted or unsubstituted $C_{3-8}$ cycloalkyl group, a substituted or unsubstituted aralkyl group, or a substituted or unsubstituted aryloxy group, Q is a substituted or unsubstituted $C_{1-10}$ alkyl group, a substituted or unsubstituted $C_{1-10}$ alkenyl group, a substituted or unsubstituted $C_{1-10}$ alkynyl group, a substituted or unsubstituted $C_{3-8}$ cycloalkyl group, a substituted or unsubstituted aralkyl group, or a substituted or unsubstituted aryl group.

13 Claims, No Drawings

INTERMEDIATES FOR DIFLUOROPROSTACYCLINS AND METHODS FOR THEIR PRODUCTION

This is a division of application Ser. No. 08/390,316 filed on Feb. 17, 1995, now U.S. Pat. No. 5,538,995.

The present invention relates to novel difluoroprostacyclins. More particularly, it relates to 7,7-difluoroprostacyclins having two fluorine atoms at the 7-position of prostacyclin.

Natural type prostacyclin ($PGI_2$) is a local hormone exhibiting strong physiological activities such as platelet aggregation inhibitory activities, vasodilation activities or cytophylatic activities, in vivo, and it is an important factor for adjusting cellular functions in vivo. However, natural type prostacyclin will be easily deactivated under neutral or acidic condition (the half-life in an aqueous solution of pH7.48 at 25° C. is 10.5 minutes), since it has a readily decomposable vinyl ether bond in its molecule. Attempts have been made to develop such prostacyclin as medicines, but due to the chemical instability, its application area as medicines has been limited in many cases. Accordingly, studies are being made to develop a prostacyclin derivative which has the same physiological activities as natural prostacyclin and which is chemically stable.

Prostacyclins having fluorine atoms at the 7-position have been reported (Japanese International Patent Application No. 501319/1981, Japanese Unexamined Patent Publications No. 165382/1982, No. 171988/1982, No. 91136/1986, No. 482/1987 and No. 9184/1993, and Japanese Examined Patent Publications No. 14030/1991, No. 47272/1991 and No. 24147/1989).

In the following description, the positional numbers for carbon atoms in prostacyclins or their intermediates will be represented by the positional numbers for carbon atoms in the corresponding natural type prostacyclin, unless otherwise specified. Accordingly, for example, the 7-position means the position corresponding to the 7-position of natural type prostacyclin irrespective of the presence or absence of an α-chain or its length.

With respect to prostacyclins having two or more fluorine atoms, Japanese International Publication No. 501319/1981 discloses prostacyclins fluorinated at the 2-position, the 4-position, the 7-position or the 10-position. However, with respect to the physical property data, the specific rotatory power is disclosed only for 10,10-difluoro-13,14-dehydroprostacyclin, and no physiological activity data is given for any compounds. Among such prostacyclins having two or more fluorine atoms, 10,10-difluoro-13,14-dehydroprostacyclin is the only compound, of which the physiological activities have been made clear. J. Fried et al. as the inventors for the invention disclosed in the above Japanese International Patent Publication No. 501319/1981, have reported on the vasodilation activities, platelet aggregation inhibitory activities, chemical stabilities, etc. in e.g. J. Med. Chem., 23, 234 (1980) Proc. Natl. Acad. Sci. U.S.A., 77, 6846 (1980) and Thromb. Res. 23, 387 (1981).

On the other hand, with respect to prostacyclins having two fluorine atoms at the 7-position, a Preparation Example for 7,7-difluoro-13,14-dehydroprostacyclin is disclosed in the above-mentioned Japanese International Patent Publication No. 501319/1981, but the synthesis used in the Example is considered to be practically really difficult to carry out, and no physical data or physiological activity data is disclosed, and so far as the present inventors are aware, there has been no further report since then. Further, among difluoroprostacyclins, there is no preparation example other than the one in which the 13- and 14-positions of the ω-chain are of a dehydro type, and no Preparation Example has been known for derivatives in which the 16- to 20-positions are other than a n-pentyl group, such as a branched alkyl group, an alkenyl group, an alkynyl group or a cycloalkyl group.

7,7-difluoro-13,14-dehydroprostacyclin disclosed in the Preparation Example of the above-mentioned Japanese International Patent Publication No. 501319/1981, is prepared in such a manner that using cyclopentadiene and dichloro ketone as starting materials, 7,7-difluoro-13,14-dehydroprostagrandin $F_2$ is firstly synthesized and then cyclized. In this method, preparation of the material i.e. 7,7-difluoro-13,14-dehydroprostagrandin $F_2$ requires a plurality of steps and is very difficult. In particular, the Wittig Reaction to prepare 7,7-difluoro-13,14-dehydroprostagrandin $F_2$ by reacting 5-triphenylphosphonopentanoic acid to the corresponding hemiacetal having two electron-withdrawing fluorine atoms as adjacent groups, will be practically difficult to obtain the desired product, since, as is different from the usual case, the yield in the reaction will remarkably be lowered by the strong electron-withdrawing effects of the fluorine atoms. Further, the cyclization reaction of 7,7-difluoro-13,14-dehydroprostagrandine $F_2$ has problems that since two electron-withdrawing fluorine atoms are present adjacent to the olefin as the reaction site, the reactivity is very low, it requires a long time for the reaction, and the yield in the reaction is low, as is different from the cyclization reaction of natural type prostagrandin $F_2$. Thus, the process is practically very difficult.

As described above, with respect to conventional 7,7-difluoroprostacyclins, no specific physical data or physiological activity data have been known, and it is hardly believable that such compounds have actually been synthesized.

The present inventors have conducted studies with an aim to actually prepare 7,7-difluoroprostacyclins and then measure their physical properties and physiological activities to study their usefulness as medicines and to find out difluoroprostacyclins which are chemically stable and which have physiological activities similar to natural type prostacyclin. As a result, the present inventors have succeeded in developing a process for producing 7,7-difluoroprostacyclins, which is different from the above-mentioned process, whereby they have succeeded in synthesizing novel difluoroprostacyclins and in discovering difluoroprostacyclins which have high physiological activities and which are chemically stable.

The present invention relates to difluoroprostacyclins and a process for their production. Further, the present invention relates to novel intermediates useful for such a process and to processes for such intermediates. Now, the basic production scheme and its general structure will be described first, and then the compounds involved in the scheme and the processes for their production will be described in detail.

Basic production scheme

The basic scheme for production of difluoroprostacyclins of the present invention is as follows:

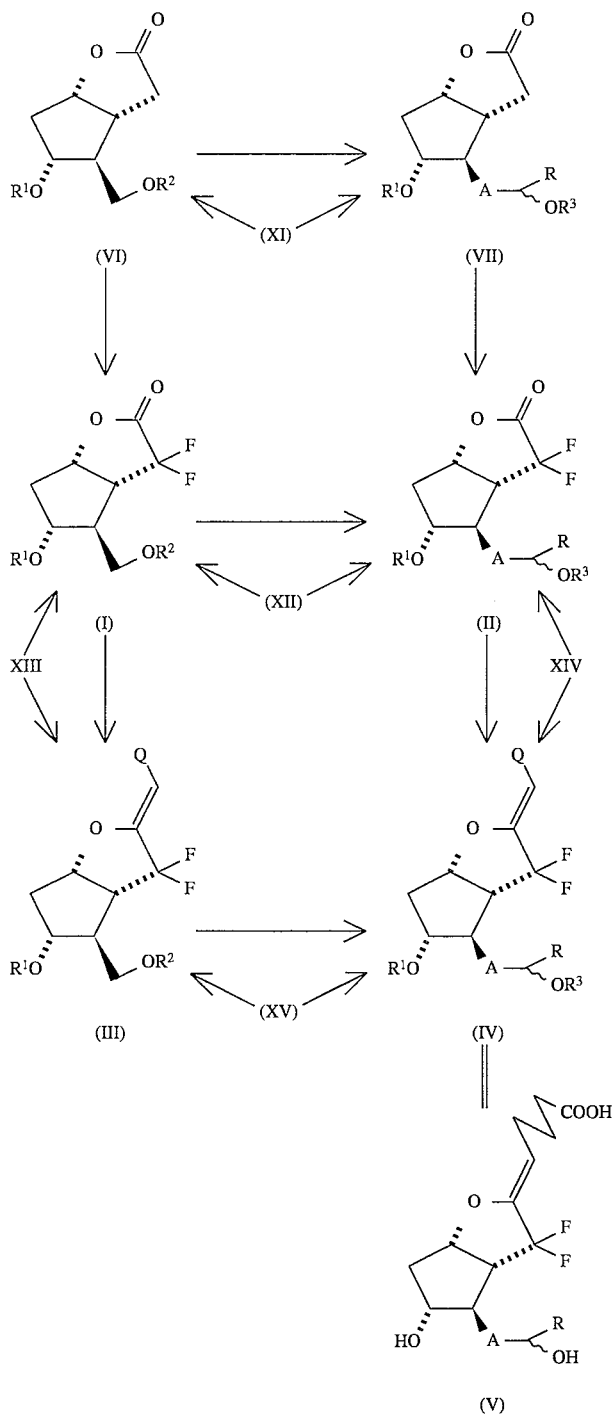

The formulas (VI) and (VII) are combined and represented by the following formula (XI). Likewise, the formulas (I) and (II) are combined and represented by the following formula (XII); the formulas (I) and (III) are combined and represented by the following formula (XIII); the formulas (II) and (IV) are combined and represented by the following formula (XIV); and the formulas (III) and (IV) are combined and represented by the following formula (XV).

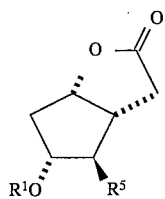

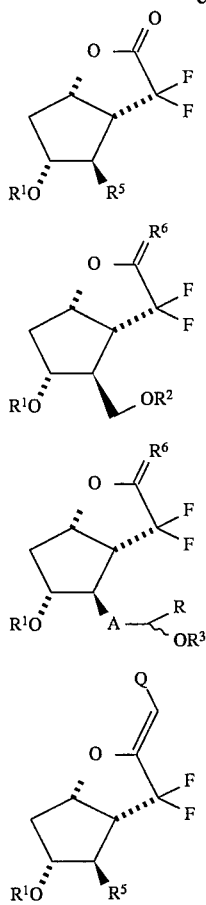

General structure of the basic production scheme

In the above production scheme, the difluoroprostacyclins of the present inventions are compounds of the formula (IV). Among the difluoroprostacyclins of the formula (IV), preferred compounds are difluoroprostacyclins of the formula (V).

The difluoroprostacyclins of the formula (IV) of the present invention can be produced by introducing the α-chain moiety to difluorolactones of the formula (II) having the ω-chain moiety introduced. Otherwise, they can be produced by introducing the ω-chain moiety to bicyclo compounds of the formula (III) having the α-chain moiety introduced. The difluorolactones of the formula (II) having the ω-chain moiety introduced, can be prepared by introducing the ω-chain moiety to difluorolactones of the formula (I). Likewise, the bicyclo compounds of the formula (III) having the α-chain moiety introduced, can be produced by introducing the α-chain moiety to the difluorolactones of the formula (I). The difluorolactones of the formula (I) are novel compounds. The difluorolactones of the formula (I) can be prepared by fluorinating lactones of the formula (VI). The difluorolactones of the formula (II) having the ω-chain moiety introduced, can be prepared by fluorinating lactones of the formula (VII) having the ω-chain moiety introduced. The lactones of the formula (VII) having the ω-chain moiety introduced, can be prepared by introducing the ω-chain moiety to lactones of the formula (VI).

Introduction of the α-chain moiety

Introduction of the α-chain moiety is meant for conversion of =O of the lactone moiety to =CH—Q. The introduction of the α-chain moiety corresponds to the step of producing two compounds of the formula (XV) in the third stage of the basic scheme from two compounds of the formula (XII) in the second stage of the basic scheme.

As a first method, an organometallic compound of the formula (VIII) is addition-reacted to a compound having a lactone structure, followed by dehydration. In this case, it is usually necessary that the hydroxyl groups in the compound having a lactone structure are protected (i.e. $R^1$, $R^2$ and $R^3$ are protecting groups).

$$(Q—CH_2)_mML_n \qquad \text{(VIII)}$$

As a second method for introducing the α-chain moiety, the desired compound can also be produced by reacting a phosphorane of the following formula (XVI).

$$Q—CH=P(R^7)_3 \qquad \text{(XVI)}$$

This second method is simpler than the above-mentioned first method and presents a high yield, and since no by-product from the metallic compound will be produced, the purification is easy. Also in the case of this second method, it is usually necessary that the hydroxyl groups in the compound having a lactone structure are protected.

Introduction of the ω-chain moiety

Introduction of the ω-chain moiety is meant for converting —$CH_2OR^2$ to —A—$CH(OR_3)$—R. The introduction of the ω-chain moiety corresponds to the step of producing two compounds of the formula (XIV) on the right hand side of the basic scheme from two compounds of the formula (XIII) on the left hand side of the basic scheme. Further, the stage of producing a compound of the formula (VII) at the upper right hand side from a compound of the formula (VI) at the upper left hand side, is also introduction of the ω-chain moiety.

As a method for this introduction, the desired compound can be produced by converting —$CH_2OR^2$ to —CHO, and reacting the product with an organic phosphonate of the formula (IX), followed by reduction. In this case, it is usually necessary that functional groups such as hydroxyl groups in the compound having —$CH_2OR^2$ are protected (i.e. $R^1$, etc. are protecting groups).

$$(R^4O)_2(P=O)CH_2C(=O)R \qquad \text{(IX)}$$

Fluorination

By fluorinating a lactone of the formula (VI) or a lactone of the formula (VII) having the ω-chain moiety introduced, it is possible to produce a difluoro compound having two fluorine atoms at the 7-position, i.e. a difluorolactone of the formula (I) or a difluorolactone of the formula (II) having the ω-chain moiety introduced. Namely, this fluorination corresponds to the step of producing two compounds of the formula (XII) in the second stage from two compounds of the formula (XI) in the first stage of the basic scheme.

This fluorination is preferably conducted by reacting an electrophilic fluorinating agent in the presence of a metal compound (X) under a basic condition.

The fluorination in the present invention can be carried out in a single step or in two steps. The fluorination in a single step means to introduce two fluorine atoms simultaneously. Likewise, the fluorination in two steps means to introduce the two fluorine atoms separately i.e. one after the other. A monofluoro compound having one fluorine atom introduced to the lactone of the formula (VI) and a monofluoro compound having one fluorine atom introduced to the lactone of the formula (VII) having the ω-chain moiety introduced, are basically known compounds. By introducing one fluorine atom to such monofluoro compounds, it is possible to obtain the corresponding difluoro compounds.

Terms

In the following description, the term "lower" for an organic group corresponds to a carbon number of from 1 to 6. A preferred lower organic group is an organic group having from 1 to 4 carbon atoms. An "alkyl group" may be a straight chain or branched, and unless otherwise specified, a lower alkyl group is preferred. Specific examples include a methyl group, an ethyl group, a propyl group, an isopropyl group, a butyl group, an isobutyl group, a t-butyl group, a pentyl group and a hexyl group. An "alkenyl group" is preferably a lower alkenyl group unless otherwise specified, more preferably a straight chain or branched alkenyl group having from 2 to 6 carbon atoms and one unsaturated group. Specific examples include a vinyl group, allyl group, a 1-propenyl group, an isopropenyl group, a 3-butenyl group, a 3-pentenyl group and a 4-hexenyl group. An "alkynyl group" is preferably a lower alkynyl group unless otherwise specified, more preferably a straight chain or branched alkynyl group having from 2 to 6 carbon atoms and one unsaturated group. Specific examples include a 1-propynyl group, a 2-propynyl group, an isopropynyl group, a 3-butynyl group, a 3-pentinyl group and a 4-hexynyl group.

As an "alkoxy group", a lower alkoxy group is preferred, and more preferred is a straight chain or branched alkoxy group having from 1 to 4 carbon atoms. Specific examples include a methoxy group, an ethoxy group, a propoxy group and a butoxy group. As an "alkoxyalkyl group", a lower alkyl group wherein the alkoxy moiety is a lower alkoxy group. Specific examples include a 2-methoxyethyl group, a 3-methoxypropyl group and a 2-ethoxyethyl group.

A "halogen atom" means a fluorine atom, a chlorine atom, a bromine atom or an iodine atom. An "aryl group" means a monovalent aromatic hydrocarbon group which may have a substituent (such as a lower alkyl group, a halogen atom, a lower alkoxy group or a lower alkylamino group), preferably a phenyl group or its derivatives. For example, a phenyl group, a tolyl group, a p-halophenyl group (such as a p-chlorophenyl group or a p-bromophenyl group), or an alkoxyphenyl group (such as a methoxyphenyl group or an ethoxyphenyl group) may be mentioned. An "aralkyl group" means an aryl-substituted alkyl group, in which the aryl group as the substituent may be as described above, and the carbon number of the alkyl group is preferably from 1 to 4. Specific examples include a benzyl group, a (2-methylphenyl)methyl group, a (3-methylphenyl)methyl group, a (3-ethylphenyl)methyl group, a benzhydryl group, a trityl group and a phenetyl group. Preferred aralkyl groups are a benzyl group and a (3-methylphenyl)methyl group.

A "protecting group" is a group for provisionally protecting a functional group having a reactivity such as a hydroxyl group, a carboxyl group or a formyl group. Functional groups are usually required to be protected in intermediates used for the production of desired final products. For example, $R^1$ or $R^3$ is usually required to be a protecting group until the final desired compound of a difluoroprostacyclin (IV) or (V) is produced. The lower alkanol residue in the lower alkanol ester in the difluoroprostacyclin (V) may be regarded as a protecting group for a carboxyl group. In the final use as a medicine, this ester is usually converted to a hydrogen atom or a cation. Known protecting groups which are commonly used can be used as such protecting groups.

A protecting group for protecting a hydroxyl group (a protecting group for a hydroxyl group) is not particularly limited. Known or well known protecting groups used as protecting groups for a hydroxyl group may be employed. Such protecting groups may be the same or different. The protecting groups for a hydroxyl group include, for example, a triorganosilyl group, an acyl group, an alkyl group, an aralkyl group or a cyclic ether group. Such protecting groups are suitably employed depending upon the particular purpose. For example, when it is required to selectively remove only one of the two protecting groups from a compound, it is preferred to use protecting groups having different reactivities. Specifically, $R^2$ and $R^3$ are preferably triorganosilyl groups, while $R^1$ is preferably a cyclic ether group or a triorganosilyl group (when other protecting groups are triorganosilyl groups, the one having a reactivity different from them).

The triorganosilyl group is a group having three organic groups such as alkyl groups, aryl groups, aralkyl groups or alkoxy groups bonded to a silicon atom. Particularly preferred is a triorganosilyl group having three groups of at least one kind selected from the group consisting of lower alkyl groups and aryl groups. Specifically, a t-butyldimethylsilyl group, a t-butyldiphenylsilyl group, a triethylsilyl group, a triphenylsilyl group or a triisopropylsilyl group may, for example, be preferred.

As the acyl group, an acetyl group or a benzoyl group is preferred, and as the cyclic ether group, a tetrahydropyranyl group or a tetrahydrofuranyl group is preferred. As the alkyl group which may have a substituent or the aralkyl group, an alkoxyalkyl group such as a methoxymethyl group, a 1-ethoxyethyl group or a 2-methoxyethoxymethyl group as well as a benzyl group, a methoxybenzyl group or a trityl group may, for example, be mentioned.

The protecting group for a hydroxyl group as mentioned above, can be converted to a hydroxyl group by a conventional method. For example, it can readily be converted to a hydroxyl group by methods disclosed in e.g. "Shinjikken Kagaku Koza 14 Syntheses and Reactions of Organic Compounds (I), (II) and (V)", published by Maruzen, and "Protective Groups in Organic Synthesis" edited by T. W. Greene, J. Wiley & Sons.

Difluorolactones (I)

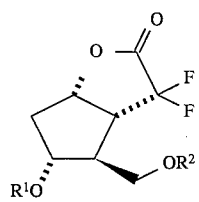

In the above formula (I), each of $R^1$ and $R^2$ which are independent of each other is a hydrogen atom or a protecting group.

The difluorolactone of the formula (I) in the present invention is a preferred compound as a starting compound of a difluoroprostacyclin of the formula (IV). In this compound, each of $R^1$ and $R^2$ may be a hydrogen atom, but is usually required to be a protecting group for the subsequent reaction. This difluorolactone of the formula (I) can be prepared by fluorinating a lactone of the formula (VI). As mentioned above, $R^1$ is preferably a cyclic ether group or a triorganosilyl group having a reactivity different from $R^2$, and $R^2$ and is preferably a triorganosilyl group or an acyl group.

As mentioned above, the difluorolactone of the formula (I) can be produced by fluorinating a lactone of the formula (VI). It is particularly preferred to produce it by the following fluorination method of introducing two fluorine atoms in one step. However, it can be produced by fluorination in two steps. Further, the difluorolactone of the formula (I) may be produced by other methods (Japanese International Patent Publication No. 501319/1981).

Details of fluorination

Now, the method for producing the difluorolactone of the formula (I) by fluorinating a lactone of the formula (VI) will be described in detail. This fluorination method can be applied also to a fluorination method for producing the difluorolactone of the formula (II) having the ω-chain moiety introduced from the lactone of the formula (VII) having the ω-chain moiety introduced. This difluoro conversion may be represented by the following formula In the following formula, $R^5$ is —$CH_2OR^2$ or —A—$CH(OR^3)$—R. The compound of the formula (XI) represents both the lactone of the formula (VI) and the lactone of the formula (VII) having the ω-chain moiety introduced. Likewise, the compound of the formula (XII) represents both the difluorolactone of the formula (I) and the difluorolactone of the formula (II) having the ω-chain moiety introduced.

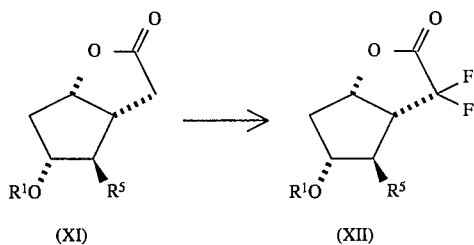

As a method for producing the difluorolactone of the formula (I) by difluorination of the lactone of the formula (VI), it is preferred to employ a method of reacting an electrophilic fluorinating agent in the presence of a metal compound (X). This difluorination reaction is preferably conducted under a basic condition and in the presence of an inert solvent. The metal compound (X) is believed to activate an active substance formed in an intermediate stage of the reaction with respect to the fluorination reaction. If the fluorination is conducted in the absence of the metal compound, a difluoro compound will not substantially form although a monofluoro compound may form.

Metal compound (X)

As the metal compound (X), an organometallic compound or a metal salt may, for example, be mentioned. As the metal in the metal compound, a metal species such as B, Mg, Al, Ca, Ti, V, Mn, Fe, Co, Ni, Cu, Zn, Zr, Sn, Ba, Hf, W, La, Ce or Sm may, for example, be mentioned. As the metal compound (X), a metal halide, an organic metal halide (particularly an alkyl metal halide), a metallocene halide, or a metal salt of trifluoromethanesulfonic acid is, for example, preferred. As the metal species, a transition metal is preferred. As specific metal compounds (X), the following metal compounds may, for example, be mentioned.

Boron trifluoride etherate, magnesium chloride, magnesium bromide, magnesium iodide, magnesium trifluoromethanesulfonate, aluminum chloride, dialkyl aluminum chloride, alkylaluminum dichloride, calcium chloride, titanium tetrachloride, titanium trichloride isopropoxide, titanium dichloride diisopropoxide, titanium chloride triisopropoxide, titanium tetrabromide, titanium tribromide isopropoxide, titanium dibromide diisopropoxide, titanium bromide triisopropoxide, titanocene dichloride, vanadium chloride, manganese dichloride, manganese dibromide, iron trichloride, iron tribromide, iron triiodide, cobalt chloride, nickel chloride, nickel bromide, copper chloride, copper bromide, copper iodide, zinc chloride, zinc bromide, zinc iodide, zinc trifluoromethanesulfonate, zirconium chloride, zirconium bromide, zirconocene dichloride, zirconocene chloride hydride, tin tetrachloride, tin dichloride, tin trifluoromethanesulfonate, ballium chloride, ballium bromide, ballium iodide, hafnium chloride, hafnocene dichloride, tangusten chloride, lanthanum chloride, cerium chloride, and samarium iodide.

The metal compound is used usually in an amount of from 0.01 to 20 equivalents, preferably from 0.1 to 10 equivalents, per equivalent of the lactone of the formula (VI).

Electrophilic fluorinating agent

The electrophilic fluorinating agent is not particularly limited. Known or well known electrophilic fluorinating agents may be employed. For example, electrophilic fluorinating agents disclosed, for example, in "Fluorine Chemistry" edited by Tomoya Kitazume, Takashi Ishihara and Takeo Taguchi and published by Kodansha Scientific, may, for example, be used. Specifically, fluorine gas, xenon fluoride, perchloryl fluoride, acetyl hypofluorite, N-fluorosulfonamides, or N-fluorosulfonimides may, for example, be mentioned. N-fluorosulfonamides or N-fluorosulfonimides are preferred. Specifically, N-fluorobenzenesulfonimide, N-fluoro-p-fluorobenzenesulfonimide, N-fluoro-o-benzenedisulfonimide, N-fluoro-p-toluenesulfonimide, N-fluoro-N-t-butylbenzenesulfonamide, N-fluoro-N-t-butyl-p-toluenesulfonamide, N-fluoro-N-methylbenzenesulfonamide, and N-fluoro-N-norbornyl-p-fluorobenzenesulfonamide are particularly preferred.

The electrophilic fluorinating agent is used usually in an amount of from 0.5 to 20 equivalents, preferably from 2 to 10 equivalents, per equivalent of the lactone of the formula (VI).

Basic condition

As the base, an amide of an alkali metal such as lithium, sodium or potassium with ammonia or a secondary amine, a hydride of an alkali metal, an alkali metal alkoxide or an organic compound of an alkali metal is, for example, preferred. Specifically, lithium amide, sodium amide, potassium amide, lithium diisopropylamide, lithium diethylamide, lithium dicyclohexylamide, lithium isopropylcyclohexylamide, lithium-2,2,6,6-tetramethylpiperidine, lithium hexamethyldisilazide, sodium diethylamide, sodium hexamethyldisilazide, potassium-3-aminopropylamide, potassium hexamethyldisilazide, lithium hydride, sodium hydride, potassium hydride, potassium t-butoxide, n-butyl lithium, s-butyl lithium, t-butyl lithium, lithium naphthalenide or lithium biphenylide may, for example, be mentioned.

The base is used usually in an amount of from 0.5 to 20 equivalents, preferably from 2 to 10 equivalents, per equivalent of the lactone of the formula (VI).

Inert solvent

As the inert solvent, an ether solvent, a hydrocarbon solvent, a polar solvent, or a solvent mixture thereof is preferred. The ether solvent may, for example, be diethyl ether, tetrahydrofuran, 1,4-dioxan, 1,2-dimethoxyethane, diglyme or t-butylmethyl ether. The hydrocarbon solvent may, for example, be hexane, toluene, benzene, pentane, xylene or petroleum ether. The polar solvent may, for example, be dimethylsulfoxide, hexamethylphosphoramide (HMPA), 1,3-dimethyl-3,4,5,6-tetrahydro-2(1H)-pyrimidinone (DMPU), 1,3-dimethyl-2-imidazolydinone (DMI), or N,N,N',N'-tetramethylethylenediamine (TMEDA). The inert solvent is used usually in an amount of from 5 to 1,000 parts by weight, preferably from 10 to 100 parts by weight, per part by weight of the lactone of the formula (VI). The reaction temperature for the above fluorination reaction is usually from −150° to +100° C., preferably from −80° to +40° C.

Monofluorinated products

A monofluorinated product of the lactone of the formula (VI) and a monofluorinated product of the lactone of the formula (VII) having the ω-chain moiety introduced are basically known compounds (Japanese Unexamined Patent Publication No. 171988/1982). By fluorinating such monofluoro compounds, it is possible to produce the corresponding difluoro compounds, i.e. the difluorolactones of the formula (I) and the difluorolactone of the formula (II) having the ω-chain moiety introduced.

The above monofluoro compounds can be produced by a conventional method. Further, according to the above-mentioned fluorination method, the above monofluoro compound can be produced under a milder condition by using a less amount of the fluorination agent, by using a fluorination agent other than those mentioned above, or by using a reactant other than the above-mentioned metal compound (X) or a catalyst. As the method for producing a difluoro compound by fluorinating the monofluorinated product, it is preferred to employ the above-mentioned fluorination method.

Difluorolactones of the formula (II) having the ω-chain moiety introduced

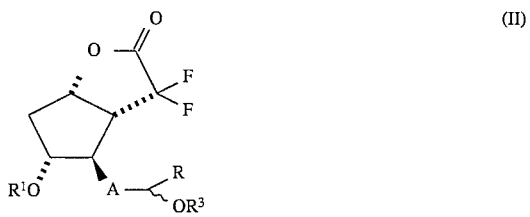

In the above formula (II), A, R, R$^3$ are as (R$^1$ is as defined above).

A: An ethylene group, a vinylene group or an ethynylene group

R: A substituted or unsubstituted $C_{1-10}$ alkyl group, a substituted or unsubstituted $C_{1-10}$ alkenyl group, a substituted or unsubstituted $C_{1-10}$ alkynyl group, a substituted or unsubstituted $C_{3-8}$ cycloalkyl group, a substituted or unsubstituted aralkyl group, or a substituted or unsubstituted aryloxy group.

R$^3$: A hydrogen atom or a protecting group for a hydroxyl group.

As A, a vinylene group or an ethynylene group is preferred, and particularly preferred is a vinylene group. OR$^3$ bonded to the carbon atom at the 15-position may be present below the paper surface or above the paper surface. In natural type PGI$_2$, the hydroxyl group bonded at the 15-position is present below the paper surface. The compound wherein this hydroxyl group is present above the paper surface, has no substantial physiological activities. However, the difluoroprostacyclins formulas (IV) and (V) of the present invention have a remarkable characteristic such that not only the compounds wherein the hydroxyl group bonded at the 15-position is present below the paper surface, but also the compounds wherein the hydroxyl group is present above the paper surface, have physiological activities.

With respect to R

R is preferably an organic group corresponding to the ω-chain moiety of natural type PGI$_2$ or an organic group corresponding to the ω-chain moiety of various PGI$_2$. Such an organic group includes, for example, a $C_{1-10}$ alkyl group, a $C_{1-10}$ alkenyl group, a $C_{1-10}$ alkynyl group, a $C_{3-8}$ cycloalkyl group, an aryloxy group having an aryl group such as a phenyl group, and such groups having various substituents. The substituents may, for example, be a cycloalkyl group and an aryl group. For example, the organic group may be a cycloalkyl group-substituted alkyl group, a cycloalkyl group-substituted alkenyl group, or an aryl group-substituted alkenyl group. Further, it may be an organic group having a carbon atom of a chain organic group substituted by an oxygen atom or a sulfur atom, or an organic group having a ring such as a cycloalkylene group or an arylene group in the chain organic group. Substituents in R include, in addition to the above-mentioned substituents, a halogen atom, an oxygen atom-containing substituent, a sulfur atom-containing substituent, a nitrogen atom-containing substituent, and others.

Among the above-mentioned various groups, a chain hydrocarbon group is preferred as R. The chain hydrocarbon group is preferably a $C_{3-8}$ alkyl group, a $C_{3-8}$ alkenyl group or a $C_{3-8}$ alkynyl group. Particularly preferred is such a group of a linear type with 5 or 6 carbon atoms or its monomethyl or dimethyl-substituted group.

When R is a chain hydrocarbon group, the carbon number of the linear moiety excluding any branch is preferably 5 or 6. Further, such a linear moiety may have one unsaturated double bond or unsaturated triple bond. The branch moiety is preferably a methyl group or an ethyl group, and particularly preferred is a methyl group. There may be two or more branched moieties, preferably one or two branched moieties. The two branched moieties may be bonded to one carbon atom. Such a branched moiety is bonded preferably at the 1- to 3-position of the chain hydrocarbon group, more preferably at the 1- or 2-position. In such a case, an unsaturated double bond or unsaturated triple bond is preferably present at 3- or subsequent position.

Specific chain hydrocarbon groups include the following groups:

A n-butyl group, a n-pentyl group, a n-hexyl group, a n-heptyl group, a n-octyl group, a n-decyl group, a 1-methylpentyl group, a 1,1-dimethylpentyl group, a 1-methylhexyl group, a 2-methylpentyl group, a 2-methylhexyl group, a 3-pentenyl group, a 1-methyl-3-pentenyl group, a 1-methyl-3-hexenyl group, a 1,1-dimethyl-3-pentenyl group, a 1,1-dimethyl-3-hexenyl group, a 2-methyl-3-pentenyl group, a 2-methyl-3-hexenyl group, a 3-pentynyl group, a 1-methyl-3-pentynyl group, a 1-methyl-3-hexynyl group, a 2-methyl-3-pentynyl group, a 2-methyl-3-hexynyl group, a 1,1-dimethyl-3-pentynyl group, and a 1,1-dimethyl-3-hexynyl group.

Among the above chain hydrocarbon groups, preferred are a 2-methylpentyl group, a 1-methylhexyl group, a 2-methylhexyl group, a 1,1-dimethylpentyl group, a 1-methyl-3-pentynyl group, a 1-methyl-3-hexynyl group, and a 1,1-dimethyl-3-hexynyl group. Particularly preferred are a 2-methylhexyl group and a 1-methyl-3-hexynyl group.

The substituted or unsubstituted cycloalkyl group for R is preferably a $C_{3-8}$ cycloalkyl group, or such a cycloalkyl group substituted by a lower alkyl group. Particularly preferred is an unsubstituted cyclopentyl group, an unsubstituted cyclohexyl group, a $C_{1-4}$ alkyl group-substituted cyclopentyl group, or a $C_{1-4}$ alkyl group-substituted cyclohexyl group.

The substituted or unsubstituted aralkyl group for R is preferably an aralkyl group containing, for example, a benzene ring, a furan ring, a thiophene ring or a naphthalene ring substituted by, for example, a lower alkyl group, a halogen atom, a halogenated alkyl group, an alkoxy group or a hydroxyl group. The carbon number of the alkyl moiety (i.e. the alkylene group) of the aralkyl group is preferably from 1 to 4. A particularly preferred aralkyl group is a $C_{1-2}$ alkyl group having a tolyl group.

The substituted or unsubstituted aryloxy group for R is preferably an aryloxy group containing, for example, a benzene ring, a furan ring, a thiophene ring or a naphthalene ring substituted, for example, by a halogen atom, a halogenated alkyl group, an alkoxy group or a hydroxyl group. Particularly preferred aryloxy group is a phenoxy group.

As R other than those described above, a $C_{1-4}$ alkyl group substituted by the above-mentioned cycloalkyl group is preferred as one type of a substituted alkyl group. As such a cycloalkyl group, a cyclopentyl group or a cyclohexyl group is preferred, and as such an alkyl group, a $C_{1-2}$ alkyl group is preferred.

Process for producing difluorolactones of the formula (II) having the ω-chain moiety introduced The difluorolactones of the formula (II) having the ω-chain moiety introduced, can be prepared by introducing the ω-chain moiety to difluorolactones of the formula (I). Otherwise, they can be prepared by fluorinating lactones of the formula (VII) having the ω-chain moiety introduced. The following method is preferred as a method for introducing the ω-chain moiety.

The lactones of the formula (VII) having the ω-chain moiety introduced, can be prepared by introducing the ω-chain moiety to the lactones of the formula (VI). The method for its introduction is also preferably the following method.

Details for introduction of the ω-chain moiety

A method for introducing the ω-chain moiety will be described in detail with reference to a process for producing a difluorolactone of the formula (II) having the ω-chain moiety introduced, from a difluorolactone of the formula (I). This method for introducing the ω-chain moiety can be applied also to a process for producing a difluoroprostacyclin of the formula (IV) from a bicyclo compound of the formula (III) having the α-chain moiety introduced. Likewise, this method for introducing the ω-chain moiety can be applied also to a process for producing a lactone of the formula (VII) having the ω-chain moiety introduced, from a lactone of the formula (VI).

Introduction of the ω-chain moiety may be represented by the following formulas, in which $R^6$ is an oxygen atom of the formula =O, or a bivalent organic group of the formula =CH—Q. The compound of the formula (XIII) represents both of the difluorolactone of the formula (I) and the bicyclo compound of the formula (III) having the α-chain moiety introduced, and the compound of the formula (XIV) represents both of the difluorolactone of the formula (II) having the ω-chain moiety introduced, and the difluoroprostacyclin of the formula (IV).

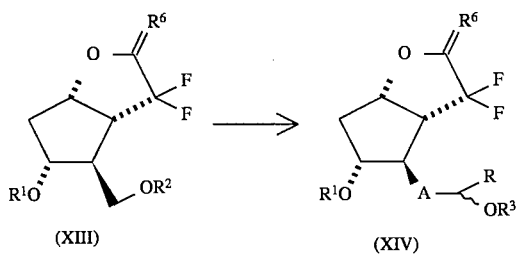

(XIII)    (XIV)

Introduction of the ω-chain moiety is preferably carried out by a Wittig-Horner-Emmons Reaction which is a known reaction. Namely, a method is preferred in which —$CH_2OR^2$ is converted to —CHO, and the product is reacted with an organic phosphonate of the formula (IX), followed by reduction. In this case, it is usually necessary that functional groups such as a hydroxyl group, etc. in the starting material are protected (i.e., $R^1$, etc. are protecting groups).

$$(R^4O)_2(P=O)CH_2(C=O)R \quad (IX)$$

In the above formula (IX), R is as defined above, and $R^4$ is a lower alkyl group. $R^4$ is preferably an alkyl group having at most 4 carbon atoms, more preferably a methyl group or an ethyl group.

Oxidation reaction

The reaction to convert —$CH_2OR^2$ to —CHO is an oxidation reaction to convert an alcohol to an aldehyde. When $R^2$ is a hydrogen atom, oxidation can directly be applied to convert —$CH_2OR^2$ to —CHO. When $R^2$ is a protecting group, $R^2$ is selectively subjected to the reaction to remove the protecting group to convert it to a hydrogen atom, and then oxidation can be conducted in the same manner. The reaction to remove the protecting group for $R^2$ differs depending upon the structure of $R^2$, and conventional methods and conditions for reactions to remove protecting groups can be applied. For example, when $R^1$ is a tetrahydropyranyl group or an acetyl group, and $R^2$ is a t-butyldimethylsilyl group, it is possible to selectively subject only $R^2$ to the reaction to remove the protective group by using tetrabutyl ammonium fluoride or HF-pyridine.

The oxidation reaction is usually carried out in the presence of e.g. dimethylsulfoxide, trifluoroacetic acid, pyridine and dicyclohexylcarbodiimide at a temperature of from $-50°$ C. to $+50°$ C., preferably from $0°$ to $+25°$ C. with stirring.

Reaction with an organic phosphonate of the formula (IX)

The reaction of the aldehyde compound formed by the oxidation reaction, with the organic phosphonate of the formula (IX) is usually preferably carried out in the presence of sodium hydride and dimethoxyethane. The reaction temperature is usually from $-50°$ C. to $+50°$ C., preferably from $0°$ C. to $+50°$ C. By this reaction, ω-chain is connected, and an unsaturated ketone will be formed at the connected portion.

Reduction reaction

The above unsaturated ketone is reduced, whereby a difluorolactone of the formula (II) having the ω-chain moiety introduced (provided that A is a vinylene group) will be formed. This reduction is usually preferably carried out in methanol in the presence of sodium borohydride and cerium trichloride. The reaction temperature is usually from $-100°$ C. to $+50°$ C., preferably from $-80°$ C. to $+10°$ C.

The compound wherein A is an ethylene group, can be prepared by reducing the unsaturated ketone by a method of reducing by means of a metal hydride such as lithium aluminum hydride or a method of hydrogenation. Otherwise, it can be prepared by converting the unsaturated ketone to a saturated ketone by a method of a 1,4-reduction reaction using a copper hydride reactant, such as (tributyltin) copper lithium hydride or copper hydride triphenylphosphine complex, followed by reduction.

The compound wherein A is an ethynylene group can be prepared by the above-mentioned reaction of the aldehyde with the organic phosphonate of the formula (IX) in the presence of a halogenating agent such as N-bromosuccinic acid imide or N-chlorosuccinic imide, and further treating with a strong base such as potassium-t-butoxide.

The bicyclo compound of the formula (III) having the α-chain moiety introduced

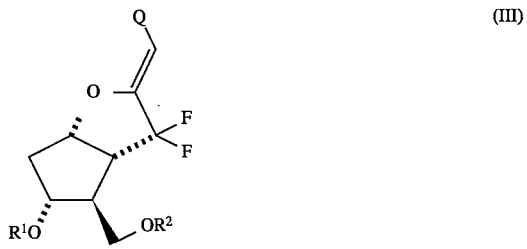

(III)

In the formula (III), Q is as defined below ($R^1$ and $R^2$ are as defined above).

Q: A substituted or unsubstituted $C_{1-10}$ alkyl group, a substituted or unsubstituted $C_{1-10}$ alkenyl group, a substituted or unsubstituted $C_{1-10}$ alkynyl group, a substituted or unsubstituted $C_{3-8}$ cycloalkyl group, substituted or unsubstituted aralkyl group, or a substituted or unsubstituted aryl group.

With respect to Q

Q is preferably an organic group corresponding to the α-chain of natural type $PGI_2$, or an organic group corresponding to the α-chain of various $PGI_2$. As such an organic group, a $C_{1-10}$ alkyl group, a $C_{1-10}$ alkenyl group, a $C_{1-10}$ alkynyl group, a $C_{3-8}$ cycloalkyl group, an aryl group such as a phenyl group, and such groups having various substituents, may be mentioned. As the substituents, a cycloalkyl group and an aryl group may be mentioned. Such groups may, for example, be a cycloalkyl group-substituted alkyl group, a cycloalkyl group-substituted alkenyl group, and an aryl group-substituted alkenyl group. Further, it may be an organic group having a carbon atom of a chain organic group substituted by an oxygen atom or a sulfur atom, or an organic group having a ring such as a cycloalkylene group or an arylene group in a chain organic group.

The substituents in Q include, in addition to the above-mentioned substituents, a halogen atom, an oxygen atom-containing substituent, a sulfur atom-containing substituent, a nitrogen atom-containing substituent, etc. Preferred Q is an organic group having a polar substituent such as a carboxyl group, or a group which can be converted to such a polar substituent, at its terminal. As the polar substituent, an oxygen atom-containing polar substituent (a carboxyl group, a formyl group and a hydroxyl group are preferred), and a group which can be converted to such a substituent, are preferred. Particularly preferred is a carboxyl group and a group which can be converted to a carboxyl group. Particularly preferred Q is an organic group represented by the after-mentioned formula -B-Z having Z as a polar substituent or a substituent which can be converted to a polar substituent.

Except for the case of the final difluoroprostacyclins of the formula (IV) having physiological activities, Q is preferably Q having a group convertible to a carboxyl group at its terminal, so that it is inert in the reactions in the course to arrive at such final compounds. Namely, Q in the organometallic compound of the formula (VIII) as well as in the bicyclo compounds of the formula (III) having the α-chain moiety introduced and the difluoroprostacyclin of the formula (IV) just synthesized, is preferably Q having a group convertible to a carboxyl group at its terminal. After the difluoroprostacyclin of the formula (IV) has been produced, this Q is converted to Q having a terminal carboxyl group. As described hereinafter, even in a case where Q is a group of the formula -B-Z, Z in the organometallic compound of the formula (VIII) is preferably a group convertible to a polar substituent, and after reaching to the difluoroprostacyclin of the formula (IV), this Z is converted to a polar substituent, particularly to a carboxyl group.

With respect to -B-Z

Q is preferably a monovalent organic group of the formula -B-Z. Z is a polar group or a group which can be converted to a polar group (such as a protected polar group), and B is a bivalent organic group. Z is preferably a carboxyl group, a group which can be converted to a carboxyl group (hereinafter referred to as an analogous group to a carboxyl group), a formyl group, a protected formyl group, a hydroxyl group, or a protected hydroxyl group. Except for the case of a final desired compound among difluoroprostacyclins of the formula (IV) (i.e. a dihalogenated prostacyclin having physiological activities), Z is preferably an analogous group to a carboxyl group. In the final desired compound, Z is most preferably a carboxyl group or a group of its salt. Usually, after synthesizing a difluoroprostacyclin of the formula (IV) wherein Z is an analogous group to a carboxyl group, which is then converted to a salt of a carboxyl group, as the case requires. Further, also when Z is a formyl group, a protected formyl group, a hydroxyl group or a protected hydroxyl group, it is preferred that Z is finally converted to a carboxyl group.

When Z is a protected formyl group, various protecting groups may be employed as the protecting group, but a protecting group such as an acetal or a thioacetal is preferred. When Z is a protected hydroxyl group, various protecting groups may be employed for the protecting group, but the above-mentioned protecting groups for a hydroxyl group are suitably employed.

When Z is an analogous group to a carboxyl group, the analogous group to a carboxyl group may, for example, be a carboxyl group neutralized with a base, an esterified carboxyl group, an orthoesterified carboxyl group, an amide-modified carboxyl group, or a carboxyl group protected by e.g. a tetrazole or a nitrile. Preferred analogous groups for a carboxyl group are an esterified carboxyl group, an orthoesterified carboxyl group, and a carboxyl group protected by a tetrazole. As the esterified carboxyl group, a carboxyl group esterified with a lower alkanol, particularly an alkoxy carbonyl group wherein the alkyl moiety is a $C_{1-4}$ alkyl group, is preferred. As the ortho esterified carboxyl group, an orthoester with a lower alkanol, or an orthoester with an alkanetriol, is preferred. As the alkanetriol, trimethylol ethane, trimethylol propane or glycerol may, for example, be mentioned. As the tetrazole, 1H-tetrazole or 2H-tetrazole is preferred.

As Z, particularly preferred is an esterified or orthoesterified carboxyl group which is stable in the reactions for preparing a difluoroprostacyclin of the formula (IV) and which is an analogous group to a carboxyl group, which can be readily converted to a carboxyl group after completion of the reactions.

When Z is the above-mentioned group other than the carboxyl group or its salt, such Z can be converted to a carboxyl group by a conventional reaction for converting to a functional group, such as by a reaction to remove a protecting group, hydrolysis or an oxidation reaction. Such a conversion can be carried out by methods disclosed, for example, in "Shinjikken Kagaku Koza, 14, Syntheses and Reactions of Organic Compounds (I), (II) and (V), Maruzen" or "Protective Groups in Organic Synthesis, edited by T. W. Greene, J. Wiley & Sons".

B is a residue obtained by removing the above Z from the above Q, and it is preferably a lower alkylene group, a lower cycloalkylene group, a lower alkylene group containing a lower cycloalkylene group (the alkylene group may be present at each side of the cycloalkylene group), a lower alkylene group containing an ether bond or a thioether bond, or a phenylene group. Particularly preferred is a $C_{3-5}$ alkylene group, a $C_{3-6}$ cycloalkylene group, a $C_{1-4}$ alkylene group containing a $C_{3-6}$ cycloalkylene group, a $C_{2-4}$ alkylene group containing one ether bond or one thioether bond in its intermediate position or a m-phenylene group. Most preferred B is a $C_{3-5}$ straight chain alkylene group. Specifically, B includes, for example, a trimethylene group, a tetramethylene group, a pentamethylene group, a cyclopropylene group, a 1,2-cyclobutylene group, a 1,3-cyclobutylene group, a 1,2-cyclopentylene group, a 1,3-cyclopentylene group, a 1,3-cyclohexylene group, a group having a methylene group bonded to one end of such a cycloalkylene group, $-CH_2OCH_2-$, $-CH_2SCH_2-$, $-(CH_2)_3OCH_2-$, —$(CH_2)_3SCH_2$—, and an m-phenylene group. Most preferred B is a trimethylene group.

Details for introduction of the α-chain moiety

Now, a method for introducing the α-chain moiety will be described in detail with reference to the process for producing a difluoroprostacyclin of the formula (IV) from a difluorolactone of the formula (II) having the ω-chain moiety introduced. This method of introducing the α-chain moiety can be applied also to other processes for introduction of the α-chain moiety. Namely, it can be applied to a process for producing a bicyclo compound of the formula (III) having the α-chain moiety introduced, from a difluorolactone of the formula (I).

In a usual addition and dehydration reactions of a lactone having no fluorine atom at the α-position of the carbonyl group, a product having the lactone ring opened, will mainly form. However, in the present reaction wherein a difluoro compound is employed, the electron-withdrawing nature of fluorine atoms is utilized, so that a bicyclo compound having the ring structure maintained, can be produced in good yield. Introduction of the α-chain moiety by this reaction is a method which does not involve a synthesis of a prostagrandin $F_2$ having a fluorine atom or a ring opening reaction between the 6- and 9-positions thereof, as was the case in the conventional method. Accordingly, the reaction is easy even if two fluorine atoms are present at the 7-position.

Introduction of the α-chain moiety can be represented by the following formulas.

In the following formulas, $R^5$ is —$CH_2OR^2$ or —A—$CH(OR^3)$—R, as mentioned above. The compound of the formula (XII) represents both of the difluorolactone of the formula (I) and the difluorolactone of the formula (II) having the ω-chain moiety introduced, as mentioned above. Likewise, the compound of the formula (XV) represents both of the bicyclo compound of the formula (III) having the α-chain moiety introduced, and the difluoroprostacyclin of the formula (IV).

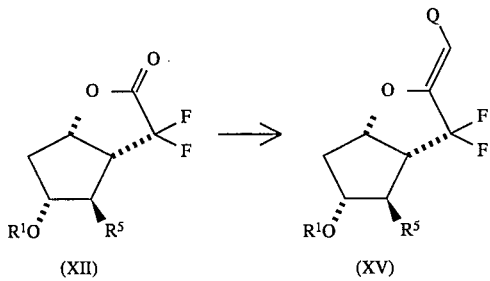

Introduction of the α-chain moiety is preferably carried out by adding an organometallic compound of the formula (VIII) to a compound having a lactone structure, followed by dehydration. As another method for introducing the α-chain moiety, a phosphorane of the following formula (XVI) is reacted for the production. This second method is considered to be advantageous over the first method of using the organometallic compound of the formula (XIII), as mentioned above.

When these reactions are carried out, the hydroxyl groups in the compound having a lactone structure are usually required to be protected (i.e. $R^1$, $R^2$ and $R^3$ are protecting groups). When free hydroxyl groups are present, by-products are likely to form, and the reaction tends to hardly proceed. Accordingly, when the difluorolactone of the formula (II) having the ω-chain moiety introduced, prepared by the above-mentioned method, has free hydroxyl groups, it is necessary to protect such free hydroxyl groups prior to this reaction. Protection of hydroxyl groups can be conducted by conventional methods. In the second method, as compared with the first method, it is less necessary to protect hydroxyl groups, and there may be a case where the reaction can be conducted even when free hydroxy groups are present.

Method 1 for introducing the α-chain moiety
Organometallic compound of the formula (XIII)

In the organometallic compound of the formula (VIII), M is a metal atom, L is a ligand to the metal, and each of m and n is an integer determined by the type of the metal atom and the type of the ligand, and m is an integer of from 1 to 8, and n is an integer of from 0 to 10. Preferably, m is from 1 to 4, more preferably from 1 to 2, and n is preferably from 0 to 4, more preferably from 0 to 2, and m+n is preferably from 1 to 3.

The metal atom M may be a metal such as lithium, sodium, potassium, magnesium, calcium, boron, aluminum or silicon, or a transition metal such as zinc, copper, iron, titanium, zirconium, manganese, tin, cobalt, nickel, cerium or samarium. Among them, lithium, sodium, magnesium, boron, aluminum, zinc or copper is preferred. Particularly preferred M is lithium, magnesium, aluminum or zinc.

The ligand L to the metal is not particularly limited, and various ligands may be employed. However, a ligand containing a halogen atom such as chlorine, bromine, iodine or fluorine, or a hetero atom such as sulfur or phosphorus, or an organic ligand such as an alkyl group, an aryl group, an alkenyl group or an alkynyl group is, for example, preferred. Particularly preferred L is chlorine, bromine, a lower alkyl group (particularly a $C_{1-4}$ alkyl group), or a phenyl group.

Addition reaction

In the addition reaction of the compound having a lactone structure with the organometallic compound of the formula (VIII), the organometallic compound of the formula (VIII) is used usually from 0.1 to 10 equivalents, preferably from 0.5 to 3 equivalents, per equivalent of the compound having a lactone structure. The reaction temperature is usually from −150° C. to +100° C., preferably from −100° C. to +40° C.

The above addition reaction can usually be conducted in the presence of a solvent. As the solvent for the reaction, an ether solvent, a hydrocarbon solvent, a polar solvent or a solvent mixture thereof is preferred. The ether solvent may, for example, be diethyl ether, tetrahydrofuran, 1,4-dioxane, dimethoxyethane, diglyme or t-butylmethyl ether; the hydrocarbon solvent may, for example, be hexane, toluene, benzene, pentane, xylene or petroleum ether; and the polar solvent may, for example, be dimethylsulfoxide, hexamethylphosphoramide (HMPA), 1,3-dimethyl-3,4,5,6-tetrahydro-2(1H)-pyrimidinone (DMPU), 1,3-dimethyl-2-imidazolidinone (DMI), or N,N,N',N'-tetramethylethylenediamine (TMEDA).

Dehydration reaction

After the addition reaction, the reaction product is subjected to a dehydration reaction to obtain a compound having the α-chain moiety introduced (both $R^1$ and $R^3$ are protecting groups).

In the dehydration reaction, various dehydrating agents may be employed. As the dehydrating agents, those disclosed, for example, in "Shinjikken Kagaku Koza, 14, Syntheses and Reactions of Organic Compounds (I)" published by Maruzen, may be employed. For example, an acid catalyst, a base catalyst, a halogenation reagent, a sulfonylation reagent, an esterification reagent, an acid anhydride, alumina, silica or an ion exchange resin may, for example, be mentioned. Specifically, a sulfonylation reagent such as methanesulfonyl chloride or toluenesulfonyl chloride, a dehydration agent such as phosphoryl chloride, thionyl chloride, oxalyl chloride, acetyl chloride, acetyl bromide, acetic anhydride, phthalic anhydride, phosphorous tribromide, N-bromosuccinimide, iodine, sulfur dioxide, phosphorus pentoxide or dicyclohexylcarbodiimide, or an acid catalyst such as p-toluenesulfonic acid, pyridinium p-toluenesulfonate or sulfuric acid is, for example, preferred.

In this dehydration reaction, the dehydration agent is used usually in an amount of from 0.1 to 10 equivalents, preferably from 1 to 5 equivalents, per equivalent of the addition reaction product. In the case where a base is used in combination, the amount of the base is usually from 0.1 to 10 equivalents, per equivalent of the dehydration agent. The reaction temperature for the dehydration reaction is usually from −80° C. to +100° C., and the reaction time is usually from 10 minutes to 10 hours.

Such a dehydration agent may be used in combination with an amine such as triethylamine, diisopropylethyl amine, tributylamine, pyridine, collidine, lutidine, 1,8-diazabicyclo[5.4.0]undeca-7-ene, 1,5-diazabicyclo[4.3.0]nona-5-ene or 1,4-diazabicyclo[2.2.2]octane, or with a base such as sodium acetate, potassium carbonate or sodium methoxide. It is particularly preferred to use a sulfonylation reagent such as methanesulfonyl chloride or toluenesulfonyl chloride as the dehydration agent in combination with an amine such as triethylamine, diisopropylethylamine, tributylamine, pyridine, collidine, lutidine, 1,8-diazabicyclo[5.4.0]undeca-7-ene, 1,5-diazabicyclo[4.3.0]nona-5-ene or 1,4-diazabicyclo[2.2.2]octane.

Method 2 for introducing the α-chain moiety Phosphoranes of the formula (XVI)

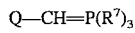  (XVI)

In the phosphorane of the formula (XVI), Q is as defined above, and $R^7$ is a monovalent organic group.

$R^7$ is preferably an aryl group which may have a substituent, an alkyl group which may have a substituent, an aralkyl group which may have a substituent, or a dialkylamino group. Particularly preferred is an aryl group which may have a substituent. As the substituent for the aryl group, a lower alkyl group, a halogen atom,. a lower alkoxy group, a lower alkylamino group, a nitro group or a hydroxyl group may, for example, be mentioned. The substituent for the alkyl group includes such substituents except for the lower alkyl group.

The aryl group which may have a substituent, may, for example, be a phenyl group, a naphthyl group, a tolyl group, a p-chlorophenyl group, a p-bromophenyl group, a p-fluorophenyl group, a p-methoxyphenyl group, a p-ethoxyphenyl group, a p-nitrophenyl group, an o-chlorophenyl group, an o-bromophenyl group, an o-fluorophenyl group, an o-methoxyphenyl group, an o-ethoxyphenyl group or an o-nitrophenyl group. Particularly preferred is a phenyl group or a tolyl group.

The alkyl group which may have a substituent, is preferably a straight chain or branched alkyl group having not more than 20 carbon atoms. Particularly preferred is a lower alkyl group. Specifically, a straight chain alkyl group such as a methyl group, an ethyl group, a n-propyl group, a n-butyl group, a n-pentyl group, a n-hexyl group, a n-heptyl group or a n-octyl group, or a branched alkyl group such as an isopropyl group, an isobutyl group, a t-butyl group or a neopentyl group is, for example, preferred. The aralkyl group which may have a substituent, is preferably an aralkyl group wherein the alkyl moiety (i.e. the alkylene group) has from 1 to 4 carbon atoms, and the aryl moiety is a phenyl group. Particularly preferred is a benzyl group, a phenetyl group or a tolyl group.

The dialkylamino group is preferably a dialkylamino group having lower alkyl groups. Specifically, a dimethylamino group, a diethylamino group or a di(n-butyl)amino group may, for example, be mentioned.

Preparation of phosphoranes of the formula (XVI)

A phosphorane of the formula (XVI) can be prepared by a conventional method from the corresponding phosphonium salt. For example, it can be prepared by reacting the following quaternary phosphonium salt ($X^-$ is an anion such as a halogen ion) with a base in an inert solvent.

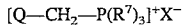

General methods for producing phosphoranes from phosphonium salts are disclosed, for example, in the above-mentioned "Shinjikken Kagaku Koza, 14. Syntheses and Reactions of Organic Compounds (I), published by Maruzen" and "Fourth Edition of Jikken Kagaku Koza, 19. Organic Synthesis I, Hydrocarbons.Halogenated Compounds, published by Maruzen". The phosphoranes of the formula (XVI) can be prepared by using such conventional methods.

A proper type of the base to be used for the preparation of a phosphorane of the formula (XVI) differs depending upon the acidity of the α-hydrogen of the phosphonium salt as the starting material of the phosphorane and the stability of the resulting phosphorane. Preferably, the following bases may be mentioned.

Sodium hydroxide, potassium hydroxide, sodium carbonate, potassium carbonate, sodium methoxide, sodium ethoxide, triethylamine, diisopropylethylamine, pyridine, N-methylmorpholine, diazabicyclononene, diazabicycloundecene, potassium t-butoxide, lithium amide, sodium amide, potassium amide, lithium diisopropyl amide, lithium diethyl amide, lithium dicyclohexyl amide, lithium isopropylcyclohexyl amide, lithium-2,2,6,6-tetramethylpiperidine, lithium hexamethyldisilazide, sodium diethylamide, sodium hexamethyldisilazide, potassium-3-aminopropylamide, potassium hexamethyldisilazide, lithium hydride, sodium hydride, potassium hydride, dimsyl sodium, n-butyl lithium, s-butyl lithium, t-butyl lithium, ethyl lithium, phenyl lithium, lithium naphthalenide, lithium biphenylide, and trityl sodium.

As the inert solvent, an ether solvent, a hydrocarbon solvent, a polar solvent, an aqueous solvent, an alcohol solvent or a solvent mixture thereof is preferred. As the ether solvent, the hydrocarbon solvent and the polar solvent, inert solvents described in the above section for "Details of fluorination" can be used. For this reaction, water, a solvent mixture of water with other solvents, and an alcohol solvent such as methanol, ethanol, t-butanol or t-amylalcohol, may also be used.

Reaction with the compound of the formula (XII)

The phosphorane of the formula (XVI) is a kind of Wittig Reaction agents. To the reaction system in which the phosphorane of the formula (XVI) has been prepared, a compound of the formula (XII) may be added, so that the two compounds are reacted to each other. Namely, a quaternary phosphonium salt is reacted with a base in an inert solvent, and without separating the resulting phosphorane of the formula (XVI), a compound of the formula (XII) is added to the reaction system, so that the two compounds can be reacted. The phosphorane of the formula (XVI) is used usually in an amount of from 0.1 to 20 equivalents, preferably from 1 to 10 equivalents, per equivalent of the compound of the formula (XII). The amount of the base is usually from 0.1 to 20 equivalents, preferably from 1 to 10 equivalents, per equivalent of the compound of the formula (XII). The amount of the inert solvent is usually from 5 to 1,000 parts by weight, preferably from 10 to 100 parts by weight, per part by weight of the compound of the formula (XII). The reaction temperature for the above Wittig Reaction is usually from −150° C. to +200° C., preferably from −80° C. to −100° C.

Difluoroprostacyclins of the formula (IV)

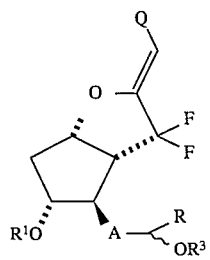

(IV)

In the formula (IV), A, Q, $R^1$ and $R^3$ are as defined above.

The difluoroprostacyclins of the formula (IV) prepared by the above described introduction of the α-chain moiety and introduction of the ω-chain moiety, have protecting groups. Accordingly, it is usually necessary to remove the protecting groups in order to obtain compounds having physiological activities. Further, when Q does not have a desired functional group in the final product, conversion to such a functional group is required. The product can be converted to a compound in which the structure of Q is different, by subjecting the product to a reaction to remove protecting groups, a reaction to convert it to a carboxylic acid by oxidation, a reaction to remove protecting groups for a hydroxyl groups, hydrolysis of an ester, or a reaction to form a salt of a carboxylic acid. For example, when Q is -B-Z wherein Z is an analogous group to a carboxyl group, a formyl group, a protected formyl group, a hydroxyl group or a protected hydroxyl group, Z can be converted to a carboxyl group by a usual reaction for conversion for a functional group, such as a reaction to remove a protecting group, hydrolysis or an oxidation reaction. Usually, protecting groups as $R^1$ and $R^3$ are removed, and Z having a polar group other than a carboxyl group, is converted to a carboxyl group. Such an reaction to remove the protective group and conversion to a carboxyl group may be conducted simultaneously or sequentially i.e. one after the other.

Accordingly, preferred difluoroprostacyclins of the formula (IV) are compounds wherein each of $R^1$ and $R^3$ is a hydrogen atom, and Q is -B-COOH, their lower alkanol esters, and their pharmaceutically acceptable salts. The lower alkanol esters and their salts may be the same as will be described hereinafter with respect to difluoroprostacyclins of the formula (V).

The difluoroprostacyclin of the formula (IV) has an asymmetric carbon in its structure and thus has various stereoisomers and optical isomers. The compounds of the present invention include, all of such stereoisomers, optical isomers and their mixtures. The same is true with respect to the difluoroprotacyclin of the formula (V).

Difluoroprostacyclins of the formula (V)

Among difluoroprostacyclins of the formula (IV), more preferred compounds are difluoroprostacyclins of the following formula (V), their lower alkanol esters, or their pharmaceutically acceptable salts.

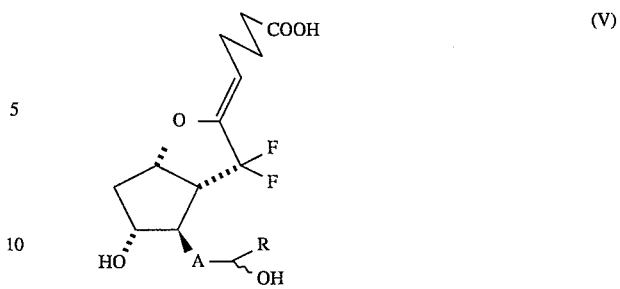

In the formula (V), A and R are as defined above. The lower alkanol ester of the difluoroprostacyclin of the formula (V) is an ester formed by the reaction of a carboxyl group of the α-chain of the difluoroprostacyclin of the formula (V) with a lower alkanol. As the lower alkanol, a lower alkanol having not more than four carbon atoms is preferred. Particularly preferred is a $C_{1-2}$ lower alkanol. Specific lower alkanols include, for example, methanol, ethanol, n-propanol, i-propanol, n-butanol, i-butanol, and t-butanol. Such a lower alkanol ester of the difluoroprostacyclin is useful as an intermediate for the synthesis of the corresponding difluoroprostacyclin, and it is believed to be useful also as a prodrug showing pysiological activities, when converted to the corresponding difluoroprostacyclin in vivo.

The pharmaceutically acceptable salt of the difluoroprostacyclin of the formula (V) is a salt of the carboxyl group moiety with a basic substance and a compound having the hydgrogen atom of a carboxyl group substituted by a cation. As such a cation, an ammonium cation such as $NH^{4+}$, tetramethyl ammonium, monomethyl ammonium, dimethyl ammonium, trimethyl ammonium, benzyl ammonium, penetyl ammonium, morpholium cation, monoethanol ammonium, triscation or piperidinium cation, an alkali metal cation such as Na+ or K+, a metal cation other than the alkali metal, such as ½ $Ca^{2+}$, ½ $Mg^{2+}$, ½ $Zn^{2+}$ or ⅓ $Al^{3+}$, may, for example, be mentioned Preferred cations are sodium ion and potassium ion.

Physical properties of difluoroprostacyclins

The present inventors have found that the difluoroprostacyclins of the formulas (IV) and (V) of the present invention have surprisingly good stability. As mentioned above, the half-life of natural type prostacyclin is about 10 minutes. Further, the half-life of 10,10-difluoro-13,14-dehydroprostacyclin disclosed in the above-mentioned Japanese International Patent Publication No. 501319/1981 is reported to be about 24 hours. The life time of the most stable compound (the one having a m-phenylene group in the α-chain) as a synthetic prostacyclin having the same vinyl ether structure, is reported to be about nine days. Whereas, the difluoroprostacyclins of the present invention have a half-life of at least about three months.

According to the study by the present inventors, the physiological activities of the difluoroprostacyclins of the present invention tend to be influenced by the type of the ω-chain. As mentioned above, in the general formulas (IV) and (V), compounds wherein A is a vinylene group have relatively high physiological activities. Among them, compounds wherein R is a branched chain hydrocarbon group have high physiological activities. Such compounds with particularly high physiological activities have substantially equal or higher physiological activities as compared with natural type prostacyclin.

7,7-difluoro-13,14-dehydroprostacyclin disclosed in the above-mentioned Japanese International Patent Publication No. 501319/1981 is a compound of of the formula (V)

wherein A is an ethynylene, and R is a n-pentyl group. The present inventors have synthesized this compound by a method as described hereinafter and measured its chemical stability and its physiological activities. As a result, it has been found that this compound has chemical stability substantially equal to other compounds (i.e. very high stability as compared with natural type prostacyclin, but its physiological activities are inadequate and substantially lower than natural type prostacyclin.

The difluoroprostacyclins of the formula (IV), the difluoroprostacyclins of the formula (V), their lower alkanol esters, or their pharmaceutically acceptable salts, of the present invention, are useful as active ingredients for preventive or therapeutic agents for diseases of circulatory organs. They are believed to be particularly useful as therapeutic agents for arteriosclerotic diseases, such as angina pectoris, cardiac infarction, cerebral infarction and hypertension, neuropathy due to diabetes, peripheral blood circulatory disorder, or scleroderma. The difluoroprostacyclins of the present invention may be administered by injection. Otherwise, by utilizing their high stability, oral administration or other methods of administration may be employed.

Now, the present invention will be described in further detail with reference to Examples. However, the present invention is by no means restricted to such specific Examples.

The scheme of Examples will be shown below. Examples 1 to 39 are preparation Examples for compounds, wherein compounds were identified by numbers. Among them, Examples 10 to 29 are Examples in which various ω-chains were introduced to Compound 9 prepared in Example 7. Examples 38 to 39 are Examples in which 7,7-difluoro-13,14-dehydroprostacyclin disclosed in the above-mentioned Japanese International Patent Publication No. 501319/1981 is prepared in accordance with the process of the present invention. Examples 40 and 41 are Examples in which the stability and the physiological activities of the synthesized compounds were measured.

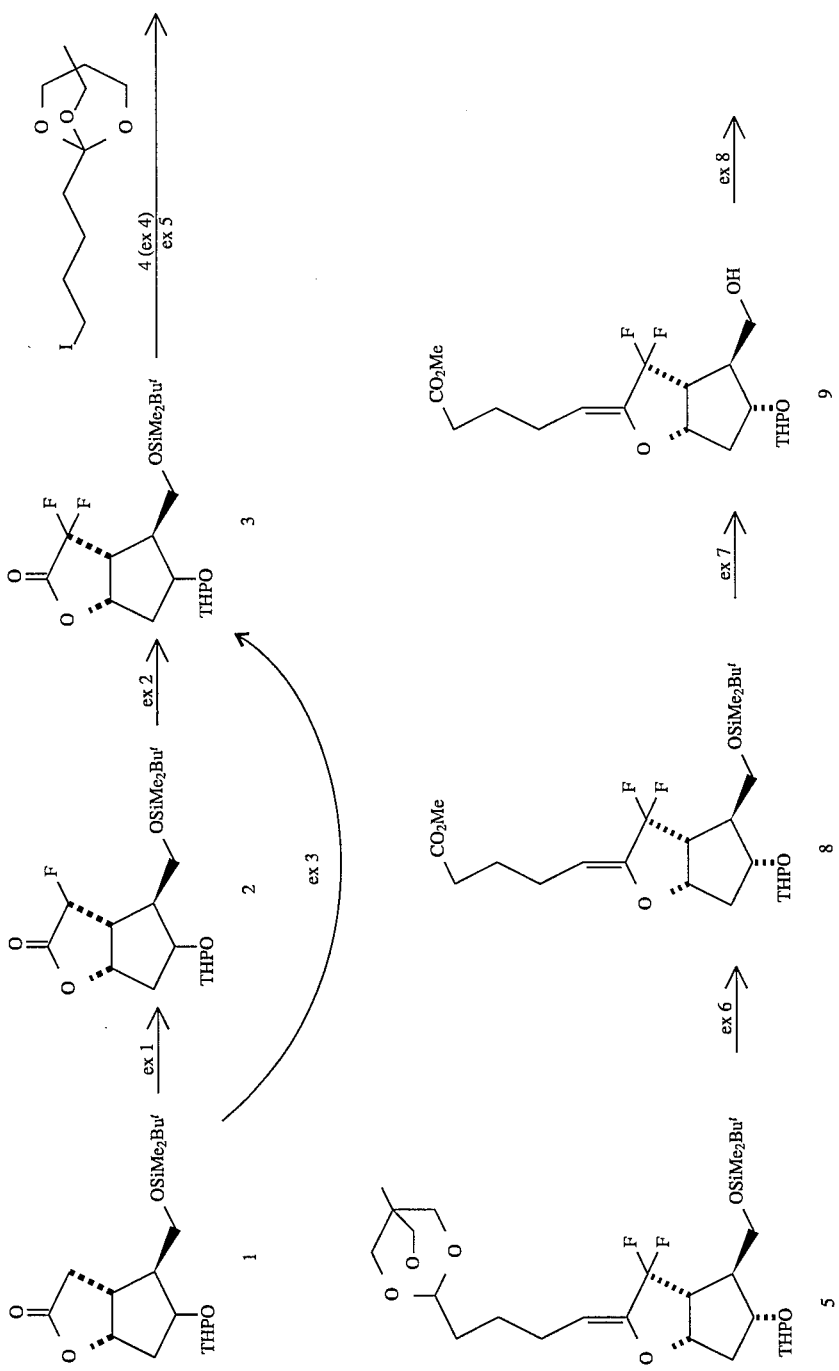

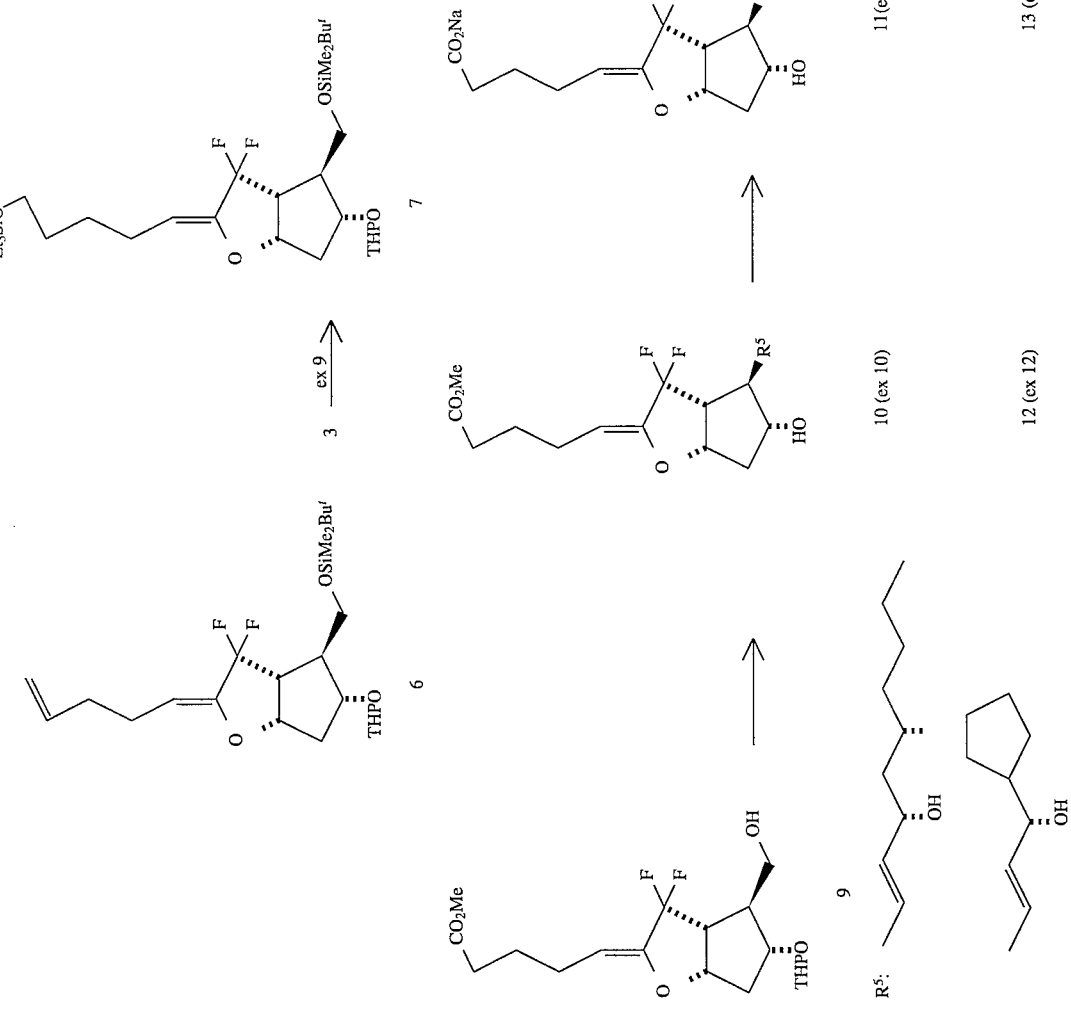

-continued
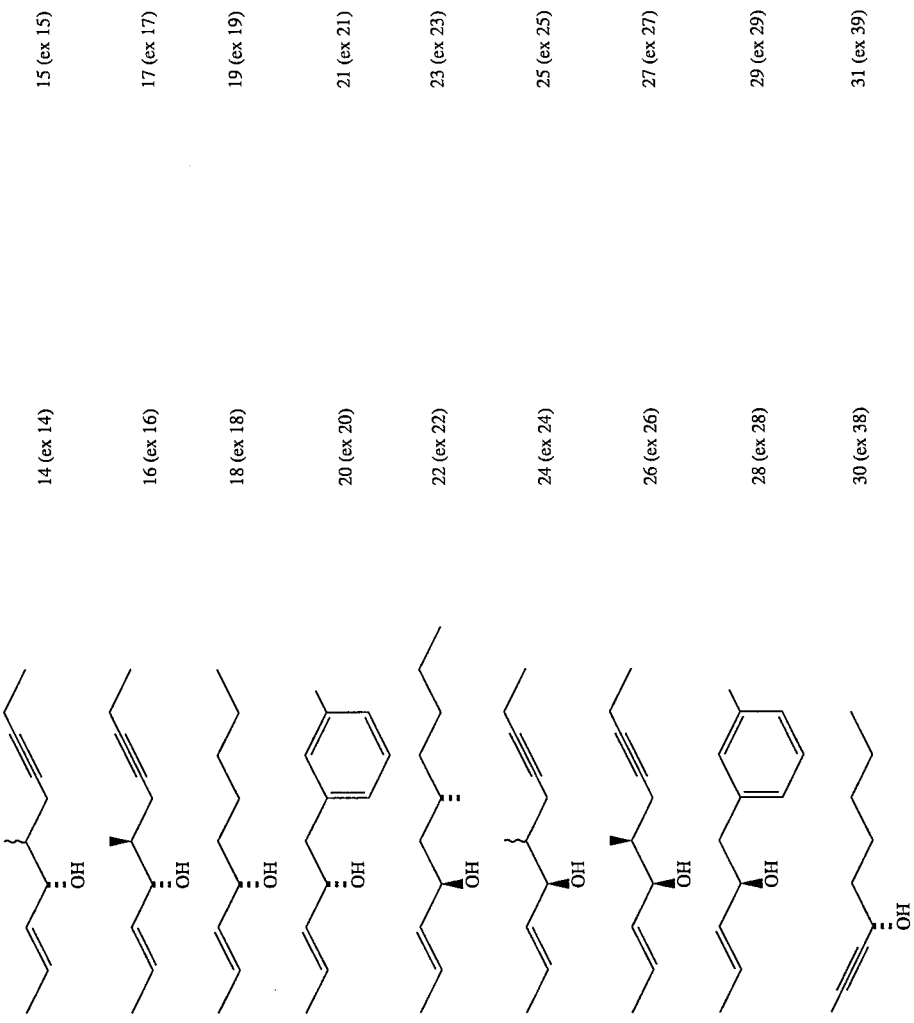

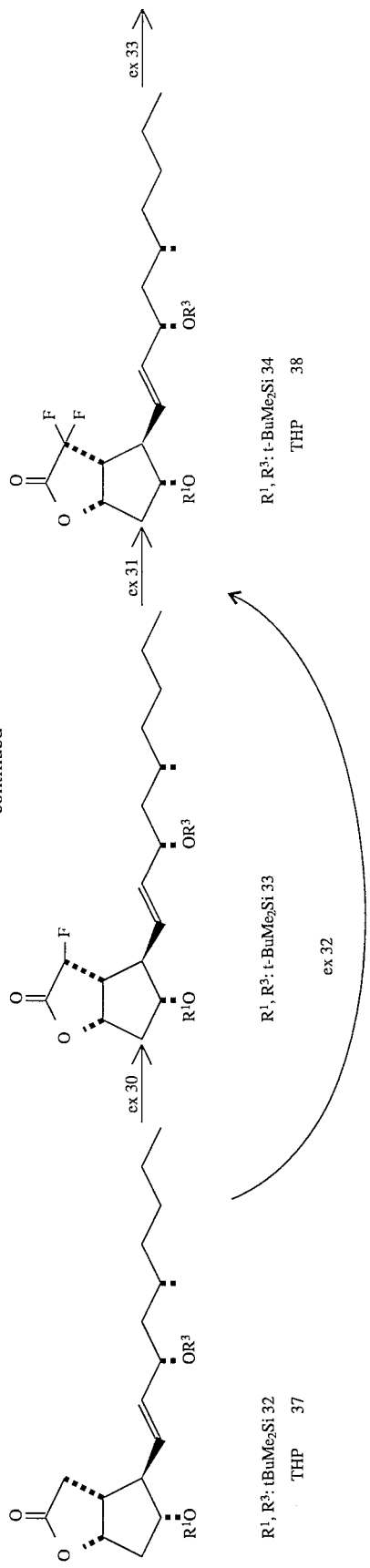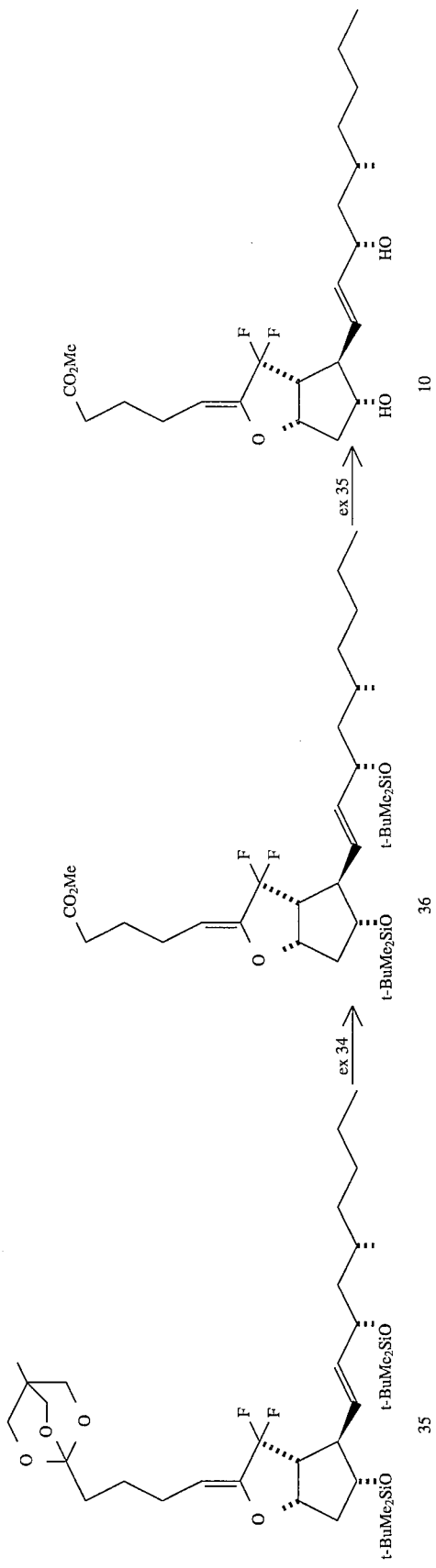

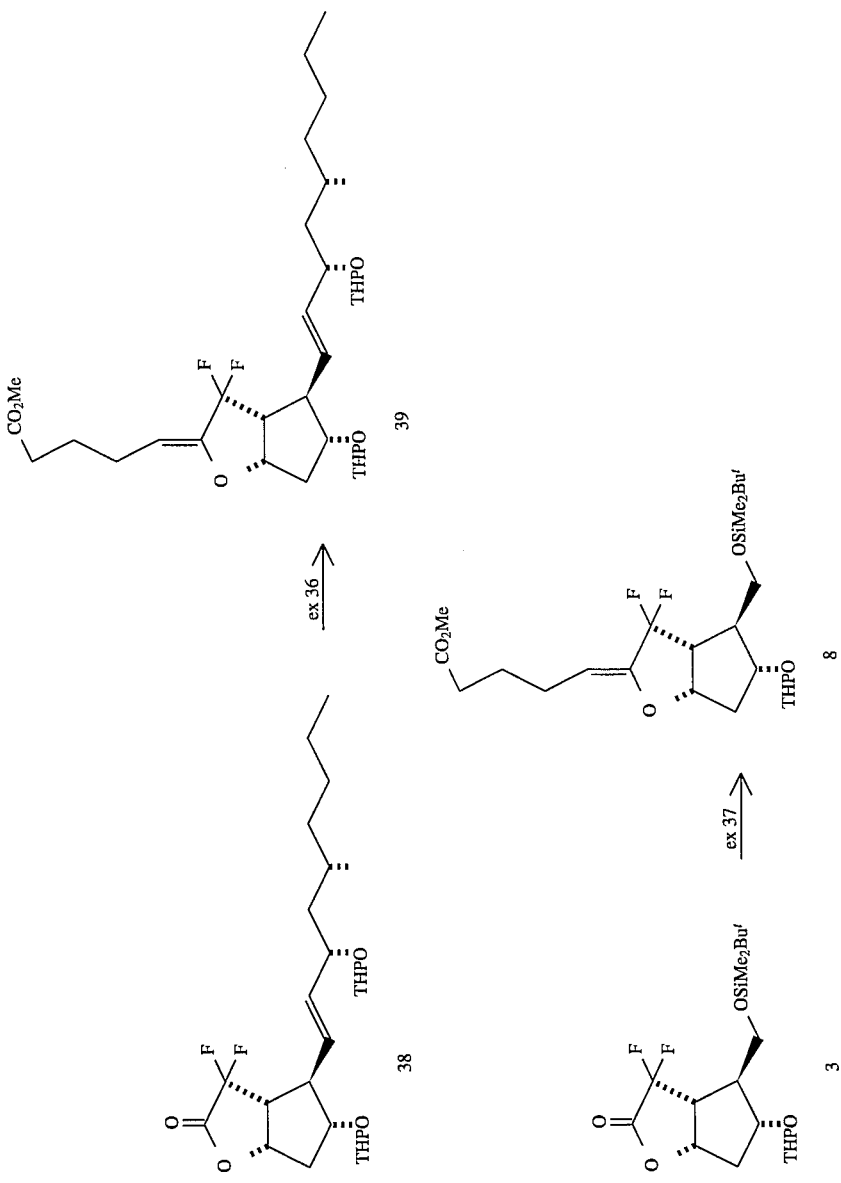

EXAMPLE 1

Preparation of (1S,5R,6R,7R)-2-oxa-4-fluoro-7-(2-tetrahydropyranyloxy)-6-(t-butyldimethylsiloxy)methylbicyclo[3.3.0]octan-3-one (Compound No. 2)

To a tetrahydrofuran (hereinafter referred to simply as THF) (90 ml) solution of hexamethyldisilazane (6.84 ml), 19.1 ml of n-butyl lithium (a 1.56M hexane solution) was added at −78° C., and the mixture was stirred for 30 minutes to obtain a lithium hexamethyldisilazide solution. To this solution, a THF (20 ml) solution of 10 g of (1S,5R,6R,7R)-2-oxa-7-(2-tetrahydropyranyloxy)-6-(t-butyldimethylsiloxy)methyl-bicyclo[3.3.0]octan-3-one (Compound 1) was dropwise added at −78° C., and the mixture was stirred for 60 minutes. Then, a THF (40 ml) solution of 9.37 g of N-fluorobenzenesulfonimide was added thereto at −78° C. The mixture was stirred at −78° C. for 60 minutes, then stirred at room temperature for 30 minutes. Then, it was poured into a saturated sodium hydrogen carbonate aqueous solution, and the mixture was extracted with ethyl acetate. The extract was purified by silica gel column chromatography (ethyl acetate:hexane=1:8 to 1:4) to obtain 9.46 g of the above-identified compound.

$^1$H-NMR (CDCl$_3$) δ (ppm): 0.05 (m, 6H), 0.88 (m, 9H), 1.4–1.8 (m, 6H), 2.0–3.1 (m, 4H), 3.4–5.3 (m, 8H).

$^{19}$F-NMR (CDCl$_3$, ppm): −179 (m).

EXAMPLE 2

Preparation of (1S,5R,6R,7R)-2-oxa-4,4-difluoro-7-(2-tetrahydropyranyloxy)-6-(t-butyldimethylsiloxy)methyl-bicyclo[3.3.0]octan-3-one (Compound 3)

To 136 mg (1 mmol) of anhydrous zinc chloride, a THF (3 ml) solution of 194 mg of (1S,5R,6R,7R)-2-oxa-4-fluoro-7-(2-tetrahydropyranyloxy)-6-(t-butyldimethylsiloxy)methyl-bicyclo[3.3.0]octan-3-one (Compound 2) prepared in Example 1, was added at room temperature, and the mixture was cooled to −78° C. Then, 1 ml of lithium diisopropylamide (a 1M THF solution) was added thereto, and the mixture was stirred for 20 minutes. To this solution, 236 mg (0.75 mmol) of N-fluorobenzenesulfonimide was added at −78° C., and the mixture was stirred for 1.5 hours. The reaction solution was poured into a saturated sodium hydrogen carbonate aqueous solution, and the mixture was extracted with ethyl acetate. The extract was purified by silica gel column chromatography to obtain 126 mg of the above-identified compound.

$^1$H-NMR (CDCl$_3$) δ (ppm): 0.06 (m, 6H), 0.89 (m, 9H), 1.2–2.3 (m, 8H), 2.6–2.7 (m, 1H), 3.09 (m, 1H), 3.4–3.9 (m, 4H), 4.23 (m, 1H), 4.64 (m, 1H), 5.12 (m, 1H).

$^{19}$F-NMR (CDCl$_3$, ppm): −94 (m), −115 (m).

Mass spectrum: 406 (M$^+$).

EXAMPLE 3

Preparation of (1S,5R,6R,7R)-2-oxa-4,4-difluoro-7-(2-tetrahydropyranyloxy)-6-(t-butyldimethylsiloxy)methyl-bicyclo[3.3.0]octan-3-one (Compound 3)

To 185 mg (1.5 mmol) of anhydrous manganese bromide, dry tetrahydrofuran (3 ml) was added. Then, a dry THF solution (3 ml) of 473 mg (1.5 mmol) of N-fluorobenzenesulfonimide was added thereto at room temperature, and the mixture was stirred for one hour. Then, a THF (3 ml) solution of 185 mg of (1S,5R,6R,7R)-2-oxa-7-(2-tetrahydropyranyloxy)-6-(t-butyldimethylsiloxy)methyl-bicyclo[3.3.01octan-3-one (Compound 1) was added thereto at −78° C., and 4 ml of potassium hexamethyldisiloxide (a 0.5M toluene solution) was added thereto. The mixture was stirred at −78° C. for one hour and at 0° C. for one hour. The reaction solution was poured into a saturated sodium hydrogen carbonate aqueous solution, and the mixture was extracted with ethyl acetate. The extract was purified by silica gel column chromatography to obtain 110 mg of the above-identified compound.

$^1$H-NMR (CDCl$_3$) δ (ppm): 0.06 (m, 6H), 0.89 (m, 9H), 1.2–2.3 (m, 8H), 2.6–2.7 (m, 1H), 3.09 (m, 1H), 3.4–3.9 (m, 4H), 4.23 (m, 1H), 4.64 (m, 1H), 5.12 (m, 1H).

$^{19}$F-NMR (CDCl$_3$, ppm): −94 (m), −115 (m).

Mass spectrum: 406 (M$^+$).

Except that the type of the metal compound was changed, preparation of the above-identified compound was conducted using the same materials under the same conditions as described above. The type of the metal compound used and the yield of the above-identified compound are shown in Table 1. The abbreviations used in the Table for metal compound reagents are as follows.

Cp$_2$ZrCl$_2$: zirconocene dichloride

Zn(OTf)$_2$: zinc trifluoromethanesulfonate

TABLE 1

| No. | Metal compound | Yield (%) |
|---|---|---|
| 1 | (Nil) | Trace |
| 2 | ZnCl$_2$ | 28 |
| 3 | ZnI$_2$ | 20 |
| 4 | Cp$_2$ZrCl$_2$ | 52 |
| 5 | Zn(OTf)$_2$ | 25 |
| 6 | CeCl$_3$ | 45 |

EXAMPLE 4

Preparation of 1-(4-iodobutyl)-4-methyl-2,6,7-trioxabicyclo[2.2.2]octane (Compound 4)

This compound was prepared as follows, in the same manner as in the method disclosed by E. J. Corey et al., Tetrahedron Lett., 24, 5571 (1983).

To a methylene chloride (20 ml) solution of 4.42 g of 3-methyl-3-hydroxymethyloxetane, 5 ml of pyridine and 12.2 g of 5-iodopentanoic acid chloride were added at 0° C., and the mixture was stirred for two hours. The reaction mixture was poured into an aqueous sodium hydrogen carbonate solution, and the mixture was extracted with methylene chloride. Then, the extract was purified by silica gel column chromatography to obtain 13.0 g of the corresponding ester. To a dry methylene chloride (20 ml) solution of 6.24 g of this ester, 0.62 ml of boron trifluoride etherate was added at −15° C., and the mixture was stirred at −15° C. for 4 hours, at 0° C. for two hours and at room temperature for one hour. After adding 2.79 ml of triethylamine at 0° C., the reaction solution was concentrated and purified by silica gel column chromatography to obtain 5.42 g of the above-identified compound.

$^1$H-NMR (CDCl$_3$) δ (ppm): 0.80 (s, 3H), 1.5–1.9 (m, 6H), 3.17 (t, J=7.2 Hz, 2H), 3.89 (s, 6H).

EXAMPLE 5

Preparation of (1S,5R,6R,7R)-2-oxa-3-{4-(4-methyl-2,6,7-trioxabicyclo[2.2.2]octanyl)butylidene}-4,4-difluoro-6-(t-butyldimethylsiloxy)methyl-7-(2-tetrahydropyranyloxy)bicyclo[3.3.0]octane (Compound 5)

A dry ethyl ether (5 ml) solution of 195 mg of 1-(4-iodobutyl)-4-methlyl-2,6,7-trioxabicyclo[2.2.2]octane (Compound 4) prepared in Example 4, was cooled to −78° C., and 0.87 ml of t-butyl lithium (a 1.48M pentane solution) was added thereto. The mixture was stirred at −78° C. for two hours. An ethyl ether solution (2 ml) of 209 mg of (1S,5R,6R,7R)-2-oxa-4,4-difluoro-7-(2-tetrahydropyranyloxy)-6-(t-butyldimethylsiloxy)methyl-bicyclo[3.3.0]octan-3-one (Compound 3) was added thereto at −78° C., and the mixture was stirred at −78° C. for one hour and at −60° C. for one hour. The reaction solution was poured into an aqueous sodium hydrogen carbonate solution, and the mixture was extracted with ethyl acetate. The extract solution was washed with a saturated sodium chloride aqueous solution and then concentrated under reduced pressure. To the residue, 2 ml of methylene chloride was added, and after adding 0.53 ml of triethylamine and 0.14 ml of methanesulfonyl chloride at 0° C., the mixture was stirred at room temperature for 1.5 hours. The mixture was poured into an aqueous sodium hydrogen carbonate solution, and the mixture was extracted with ethyl acetate. The extract solution was concentrated under reduced pressure and purified by silica gel column chromatography (ethyl acetate:hexane=1:30 to 1:10) to obtain 263 mg of the above-identified compound.

$^1$H-NMR (CDCl$_3$) δ (ppm): 0.05 (m, 6H), 0.8–2.9 (m, 28H), 3.4–4.7 (m, 14H).

$^{19}$F-NMR (CDCl$_3$, ppm): −83 (m), −115 (m).

EXAMPLE 6

Preparation of methyl 5-[(1S,5R,6R,7R)-2-oxa-4,4-difluoro-7-(2-tetrahydropyranyloxy)-6-(t-butyldimethylsiloxy)methyl-bicyclo[3.3.0]octan-3-ylidene]pentanoate (Compound 8)

To a 1,2-dimethoxyethane (5 ml) solution of 263 mg of (1S,5R,6R,7R)-2-oxa-3-{4-(4-methyl-2,6,7-trioxabicyclo[2.2.2]octanyl)butylidene{-4,4-difluoro-6-(t-butyldimethylsiloxy)methyl-7-(2-tetrahydropyranyloxy)bicyclo[3.3.0]octane (Compound 5) prepared in Example 5, 0.5 ml of a 10% sodium hydrogen sulfate aqueous solution was added at 0° C., and the mixture was stirred for 30 minutes. The mixture was poured into an aqueous sodium hydrogen carbonate solution, and the mixture was extracted with ethyl acetate. The extract solution was concentrated under reduced pressure. To the residue, 5 ml of methanol and 136 mg of potassium carbonate were added, and the mixture was stirred at room temperature for two hours. The mixture was poured into an aqueous sodium hydrogen carbonate solution, and the mixture was extracted with ethyl acetate-hexane (1:1). The extract solution was concentrated under reduced pressure and purified by silica gel column chromatography (ethyl acetate:hexane=1:30 to 1:10) to obtain 191 mg of the above-identified compound.

$^1$H-NMR (CDCl$_3$) δ (ppm): 0.05 (m, 6H), 0.8–2.9 (m, 25H), 3.67 (s, 3H), 3.4–4.7 (m, 8H).

$^{19}$F-NMR (CDCl$_3$, ppm): −83 (m), −115 (m).

EXAMPLE 7

Preparation of methly 5-[(1S,5R,6R,7R)-2-oxa-4,4-difluoro-7-(2-tetrahydropyranyloxy)-6-hydroxymethyl-bicyclo[3.3.0]octan-3-ylidene]pentanoate (Compound 9)

To a THF (10 ml) solution of 340 mg of methyl 5-[(1S,5R,6R,7R)-2-oxa-4,4-difluoro-7-(2-tetrahydropyranyloxy)-6-(t-butyldimethylsiloxy)methyl-bicyclo[3.3.0]octan-3-ylidene]pentanoate (Compound 8) prepared in Example 6, 780 µl of tetrabutyl ammonium fluoride (a 1M THF solution) was added at 0° C. The mixture was stirred at room temperature for two hours. Then, the solvent was removed, and the residue was purified by silica gel column chromatography (methylene chloride:methanol=20:1) to obtain 150 mg of the above-identified compound.

$^1$H-NMR (CDCl$_3$) δ (ppm): 1.3–2.9 (m, 16H), 3.67 (s, 3H), 3.4–4.7 (m, 8H).

$^{19}$F-NMR (CDCl$_3$, ppm): −83 (m), −115 (m).

EXAMPLE 8

Preparation of (1S,5R,6R,7R)-2-oxa-3-(1,4-pentadienylidene)-4,4-difluoro-7-(2-tetrahydropyranyloxy)-6-(t-butyldimethylsiloxy)methyl-bicyclo[3.3.0]octane (Compound 6)

To an ethyl ether (10 ml) solution of 550 mg of (1S,5R,6R,7R)-2-oxa-4,4-difluoro-7-(2-tetrahydropyranyloxy)-6-(t-butyldimethylsiloxy)methyl-bicyclo[3.3.0]octan-3-one (Compound 3), a Grignard solution prepared from 0.20 ml of 5-bromo-1-pentene and 48 mg of magnesium in dry ethyl ether, was added at −78° C. The mixture was stirred for one hour. The reaction solution was poured into a saturated sodium hydrogen carbonate aqueous solution, and the mixture was extracted with ethyl acetate. The extract was concentrated under reduced pressure. Then, 10 ml of methylene chloride, 0.70 ml of triethylamine and 0.195 ml of methanesulfonyl chloride were added thereto at 0° C. Then, the mixture was stirred at room temperature for 1.5 hours. The mixture was poured into an aqueous sodium hydrogen carbonate solution, and the mixture was extracted with ethyl acetate. The extract solution was concentrated under reduced pressure and purified by silica gel column chromatography (ethyl acetate:hexane=1:30 to 1:20) to obtain 0.22 g of the above-identified compound.

$^1$H-NMR (CDCl$_3$) δ (ppm): 0.06–0.08 (m, 6H), 0.8–0.9 (m, 9H), 1.1–2.9 (m, 14H), 3.4–5.8 (m, 11H).

$^{19}$F-NMR (CDCl$_3$, ppm): −83 (m), −115 (m).

EXAMPLE 9

Preparation of (1S,5R,6R,7R)-2-oxa-3-(5-triethylsiloxybentylidene)-4,4-difluoro-7-(2-tetrahydropyranyloxy)-6-(t-butyldimethylsiloxy)methyl-bicyclo[3.3.0]octane (Compound 7)

The above-identified compound was prepared in the same manner as in Example 5 using (1S,5R,6R,7R)-2-oxa-4,4-difluoro-7-(2-tetrahydropyranyloxy)-6-(t-butyldimethylsiloxy)methyl-bicyclo[3.3.0]octan-3-one (Compound 3) and 5-iodopentanol triethylsilyl ether.

$^1$H-NMR (CDCl$_3$) δ (ppm): 0.05 (s, 6H), 0.5–1.0 (m, 24H), 1.1–2.9 (m, 16H), 3.4–4.7 (m. 9H).

$^{19}$F-NMR (CDCl$_3$, ppm): −83 (m), −115 (m).

EXAMPLE 10

Preparation of methyl 5-[(1S,5R,6R,7R)-2-oxa-4,4-difluoro-7-hydroxy-6-{(3S,5S)-3-hydroxy-5-methyl-E-1-nonenyl}bicyclo[3.3.0]octan-3-ylidene]pentanoate compound 10)

To a benzene (3 ml) solution of 150 mg of methyl 5-[(1S,5R,6R,7R)-2-oxa-4,4-difluoro-7-(2-tetrahydropyranyloxy)-6-hydroxymethyl-bicyclo[3.3.0]octan-3-ylidene] pentanoate (Compound 9) prepared in Example 7, 29 µl of pyridine, 30 µl of dimethyl sulfoxide, 4 µl of trifluoroacetic acid and 217 mg of dicyclohexylcarbodiimide were added, and the mixture was stirred at room temperature for one hour. Insoluble materials were filtered off, and the filtrate was washed with water and concentrated to obtain a crude product of the corresponding aldehyde.

To a 1,2-dimethoxyethane (5 ml) solution of 235 mg of dimethyl (4S)-4-methyl-2-oxooctanyl phosphonate, 37 mg of sodium hydride was added, and the mixture was stirred for 10 minutes. To this solution, the above-mentioned 1,2-dimethoxyethane (3 ml) solution of the crude product of the aldehyde was added at 0° C., and the mixture was stirred at room temperature for 30 minutes. Then, the mixture was poured into an aqueous sodium chloride solution, and the mixture was extracted with ethyl acetate. The extract was concentrated by drying and purified by silica gel column chromatography (ethyl acetate:hexane=1:4 to 1:1) to obtain 120 mg of the corresponding nonene. To this methanol (5 ml) solution, 102 mg of cerium chloride heptahydrate and 15 mg of sodium borohydride were added at −40° C., and the mixture was stirred at −40° C. for 10 minutes and at 0° C. for 30 minutes. Then, the mixture was poured into a saturated sodium hydrogen carbonate aqueous solution, and the mixture was extracted with ethyl acetate.

After concentration, the residue was dissolved in methanol (5 ml), and 5 mg of p-toluenesulfonic acid monohydrate was added thereto at 0° C. The mixture was stirred at room temperature for one hour. Methanol was distilled off, and then a saturated sodium hydrogen carbonate aqueous solution and ethyl acetate were added. The mixture was extracted. The extract solution was concentrated by drying and purified by silica gel column chromatography (methylene chloride:acetone=1:2) to obtain 39 mg of the above-identified compound.

$^1$H-NMR (CDCl$_3$) δ (ppm): 0.8–3.0 (m, 25H), 3.4–5.2 (m, 6H), 6.2–6.8 (m, 2H).

$^{19}$F-NMR (CDCl$_3$, ppm): −179 (m).

EXAMPLE 11

Preparation of sodium 5-[(1S,5R,6R,7R)-2-oxa-4,4-difluoro-7-hydroxy-6-{(3S,5S)-3-hydroxy-5-methyl-E-1-nonenyl}bicyclo[3.3.0]octan-3-ylidene]pentanoate (Compound 11)

To an ethanol (8 ml) solution of 139 mg of methyl 5-[(1S,5R,6R,7R)-2-oxa-4,4-difluoro-7-hydroxy-6-{(3S,5S)-3-hydroxy-5-methyl-E-1-nonenyl}bicyclo[3.3.0]octan-3-ylidene]pentanoate (Compound 10) prepared in Example 10, 3.39 ml of 0.1N sodium hydroxide was added, and the mixture was stirred at room temperature for 14 hours. The mixture was concentrated under reduced pressure to obtain 125 mg of the above-identified compound.

$^1$H-NMR (D$_2$O) δ (ppm): 0.8–2.9 (m, 25H), 3.7–4.3 (m, 2H), 4.5–5.0 (m, 2H), 5.5–5.7 (m, 2H).

$^{19}$F-NMR (D$_2$O, ppm): −84 (dd, J=17, 250 Hz), −117 (d, J=250 Hz).

EXAMPLE 12

Preparation of methyl 5-[(1S,5R,6R,7R)-2-oxa-4,4-difluoro-7-hydroxy-6-{(3S)-3-cyclopentyl-3-hydroxy-E-1-propenyl}bicylco[3.3.0]octan-3-ylidene] pentanoate (Compound 12)

The above-identified compound was prepared by the same method as in Example 10 using methyl 5-[(1S,5R,6R,7R)-2-oxa-4,4-difluoro-7-(2-tetrahydropyranyloxy)-6-hydroxymethyl-bicyclo[3.3.0]octan-3-ylidene]pentanoate (Compound 9) prepared in Example 7 and dimethyl 2-oxo-2-cyclopentylethyl phosphonate.

$^1$H-NMR (CDCl$_3$) δ (ppm): 1.1–2.7 (m, 19H), 3.67 (s, 3H), 3.8–4.3 (m, 2H), 4.7–4.9 (m, 2H), 5.4–5.7 (m, 2H).

$^{19}$F-NMR (CDCl$_3$, ppm): −84 (dd, J=17, 250 Hz), −117 (d, J=250 Hz).

Mass spectrum: 401 (M$^+$+1).

EXAMPLE 13

Preparation of sodium 5-[(1S,5R,6R,7R)-2-oxa-4,4-difluoro-7-hydroxy-6-{(3S)-3-cyclopentyl-3-hydroxy-E-1-propenyl}bicylco[3.3.0]octan-3-ylidene] pentanoate (Compound 13)

The above-identified compound was prepared by the same method as in Example 11 using methyl 5-[(1S,5R,6R,7R)-2-oxa-4,4-difluoro-7-hydroxy-6-{(3S)-3-cyclopentyl-3-hydroxy-E-1-propenyl}bicyclo[3.3.0]octan-3-ylidene]pentanoate (Compound 12) prepared in Example 12.

$^1$H-NMR (D$_2$O) δ (ppm): 1.0–2.9 (m, 19H), 3.7–4.3 (m, 2H), 4.5–5.0 (m, 2H), 5.4–5.7 (m, 2H).

$^{19}$F-NMR (D$_2$O, ppm): −84 (dd, J=17, 250 Hz), −117 (d, J=250 Hz).

EXAMPLE 14

Preparation of methyl 5-[(1S,5R,6R,7R)-2-oxa-4,4-dilufuro-7-hydroxy-6-{(3S,4RS)-3-hydroxy-4-methyl-E-1-nonen-6-ynyl}bicyclo[3.3.0]octan-3-ylidene]pentanoate (Compound 14)

The above-identified compound was prepared by the same method as in Example 10 using methyl 5-[(1S,5R,6R,7R)-2-oxa-4,4-difluoro-7-(2-tetrahydropyranyloxy)-6-hydroxymethyl-bicyclo[3.3.0]octan-3-ylidene]pentanoate (Compound 9) prepared in Example 7 and dimethyl 3-methyl-2-oxo-5-octynyl phosphonate.

$^1$H-NMR (CDCl$_3$) δ (ppm): 0.8–2.8 (m, 21H), 3.67 (s, 3H), 3.9–4.3 (m, 2H), 4.7–4.9 (m, 2H), 5.4–5.7 (m, 2H).

$^{19}$F-NMR (CDCl$_3$, ppm): −84 (m), −117 (m).

Mass spectrum: 427 (M$^+$+1).

EXAMPLE 15

Preparation of sodium 5-[(1S,5R,6R,7R)-2-oxa-4,4-difluoro-7-hydroxy-6-{(3S,4RS)-3-hydroxy-4-methyl-E-1-nonen-6-ynyl}bicyclo-[3.3.0]octan-3-ylidene]pentanoate (Compound 15).

The above-identified compound was prepared by the same method as in Example 11 using methyl 5-[(1S,5R,6R,7R)-2-oxa-4,4-difluoro-7-hydroxy-6-{(3S,4RS)-3-hydroxy-4- methyl-E-1-nonen-6-ynyl}bicyclo[3.3.0]octan-3-ylidene]
pentanoate (Compound 14) prepared in Example 14.

$^1$H-NMR (D$_2$O) δ (ppm): 0.7–2.8 (m, 21H), 3.7–4.3 (m, 2H), 4.5–5.0 (m, 2H), 5.3–5.7 (m, 2H).

$^{19}$F-NMR (D$_2$O, ppm): −84 (m), −117 (m).

EXAMPLE 16

Preparation of methyl 5-[(1S,5R,6R,7R)-2-oxa-4,4-difluoro-7-hydroxy-6-{(3S,4S)-3-hydroxy-4-methyl-E-1-nonen-6-ynyl}bicyclo-[3.3.0]octan-3-ylidene]pentanoate (Compound 16)

The above-identified compound was prepared by the same method as in Example 10 using methyl 5-[(1S,5R,6R,7R)-2-oxa-4,4-difluoro-7-(2-tetrahydropyranyloxy)-6-hydroxymethyl-bicyclo[3.3.0]octan-3-ylidene]pentanoate (Compound 9) prepared in Example 7 and dimethyl (3S)-3-methyl-2-oxo-5-octynyl phosphonate.

$^1$H-NMR (CDCl$_3$) δ (ppm): 0.8–2.8 (m, 21H), 3.67 (s, 3H), 3.9–4.3 (m, 2H). 4.7–4.9 (m, 2H), 5.4–5.7 (m, 2H).

$^{19}$F-NMR (CDCl$_3$, ppm): −84 (dd, J=17, 249 Hz), −117 (d, J=250 Hz).

Mass spectrum: 427 (M$^+$+1).

EXAMPLE 17

Preparation of sodium 5-[(1S,5R,6R,7R)-2-oxa-4,4-difluoro-7-hydroxy-6-{(3S,4S)-3-hydroxy-4-methyl-E-1-nonen-6-ynyl}bicyclo[3.3.0]octan-3-ylidene]pentanoate (Compound 17)

The above-identified compound was prepared by the same method as in Example 11 using methyl 5-[(1S,5R,6R,7R)-2-oxa-4,4-difluoro-7-hydroxy-6-{(3S,4S)-3-hydroxy-4-methyl-E-1-nonen-6-ynyl}bicyclo[3.3.0]octan-3-ylidene]pentanoate (Compound 16) prepared in Example 16.

$^1$H-NMR (D$_2$O) δ (ppm): 0.7–2.8 (m, 21H), 3.7–4.3 (m, 2H), 4.5–5.0 (m, 2H), 5.3–5.7 (m, 2H).

$^{19}$F-NMR (D$_2$O, ppm): −84 (dd, J=17, 250 Hz), −117 (d, J=250 Hz).

EXAMPLE 18

Preparation of methyl 5-[(1S,5R,6R,7R)-2-oxa-4,4-difluoro-7-hydroxy-6-{(3S)-3-hydroxy-E-1-octenyl}bicyclo[3.3.0]octan-3-ylidene]pentanoate (Compound 18)

The above-identified compound was prepared by the same method as in Example 10 using methyl 5-[(1S,5R,6R,7R)-2-oxa-4,4-difluoro-7-(2-tetrahydropyranyloxy)-6-hydroxymethyl-bicyclo[3.3.0]octan-3-ylidene]pentanoate (Compound 9) prepared in Example 7 and dimethyl 2-oxoheptynyl phosphonate.

$^1$H-NMR (CDCl$_3$) δ (ppm): 0.9–2.7 (m, 21H), 3.67 (s, 3H), 3.9–4.3 (m, 2H), 4.7–4.9 (m, 2H), 5.5–5.7 (m, 2H).

$^{19}$F-NMR (CDCl$_3$, ppm): −84 (dd, J=16, 249 Hz), −117 (d, J=249 Hz).

Mass spectrum: 403 (M$^+$+1).

EXAMPLE 19

Preparation of sodium 5-[(1S,5R,6R,7R)-2-oxa-4,4-difluoro-7-hydroxy-6-{(3S)-3-hydroxy-E-1-octenyl}bicyclo[3.3.0]octan-3-ylidene]pentanoate (Compound 19)

The above-identified compound was prepared by the same method as in Example 11 using methyl 5-[(1S,5R,6R,7R)-2-oxa-4,4-difluoro-7-hydroxy-6-{(3S)-3-hydroxy-E-1-octenyl}bicyclo[3.3.0]octan-3-ylidene]pentanoate (Compound 18) prepared in Example 18.

$^1$H-NMR (D$_2$O) δ (ppm): 0.8–2.9 (m, 21H), 3.7–4.3 (m, 2H), 4.5–5.0 (m, 2H), 5.4–5.7 (m, 2H).

$^{19}$F-NMR (D$_2$O, ppm): −84 (dd, J=17, 250 Hz), −117 (d, J=250 Hz).

EXAMPLE 20

Preparation of methyl 5-[(1S,5R,6R,7R)-2-oxa-4,4-difluoro-7-hydroxy-6-{(3S)-3-hydroxy-4-(3-methylphenyl)-E-1-butenyl}bicyclo[3.3.0]octan-3-ylidene]pentanoate (Compound 20)

The above-identified compound was prepared by the same method as in Example 10 using methyl 5-[(1S,5R,6R,7R)-2-oxa-4,4-difluoro-7-(2-tetrahydropyranyloxy)-6-hydroxymethyl-bicyclo[3.3.0]octan-3-ylidene]pentanoate (Compound 9) prepared in Example 7 and dimethyl 2-oxo-3-(3-methylphenyl)propyl phosphonate.

$^1$H-NMR (CDCl$_3$) δ (ppm): 1.4–2.9 (m, 12H), 2.33 (m, 3H), 3.67 (S, 3H), 3.89 (m, 1H), 4.32 (m, 1H), 4.7–4.9 (m, 2H), 5.5–5.8 (m, 2H), 7.0–7.2 (m, 4H)

$^{19}$F-NMR (CDCl$_3$, ppm): −84 (dd, J=12, 253 Hz), −116 (d, J=253 Hz)

EXAMPLE 21

Preparation of sodium 5-[(1S,5R,6R,7R)-2-oxa-4,4-difluoro-7-hydroxy-6-{(3S)-3-hydroxy-4-(3-methylphenyl)-E-1-butenyl}bicyclo[3.3.0]octan-3-ylidene]pentanoate (Compound 21)

The above-identified compound was prepared by the same method as in Example 11 using methyl 5-[1S,5R,6R,7R)-2-oxa-4,4-difluoro-7-hydroxy-6-{(3S)-3-hydroxy-4-(3-methylphenyl)-E-1-butenyl}bicyclo[3.3.0]octan-3-ylidene]pentanoate (Compound 20) prepared in Example 20.

$^1$H-NMR (D$_2$O) δ (ppm): 1.4–2.9 (m, 15H), 3.8–4.4 (m, 2H), 4.7–4.9 (m, 2H), 5.5–5.8 (m, 2H), 7.0–7.2 (m, 4H)

$^{19}$F-NMR (D$_2$O, ppm): −84 (dd, J=12, 253 Hz), −116 (d, J=253 Hz)

EXAMPLE 22

Preparation of methyl 5-[(1S,5R,6R,7R)-2-oxa-4,4-difluoro-7-hydroxy-6-{(3R,5S)-3-hydroxy-5-methyl-E-1-nonenyl}bicyclo[3.3.0]octan-3-ylidene]pentanoate (Compound 22)

The above-identified compound was prepared by the same method as in Example 10 using methyl 5-[(1S,5R,6R,7R)-2-oxa-4,4-difluoro-7-(2-tetrahydropyranyloxy)-6-hydroxymethyl-bicyclo[3.3.0]octan-3-ylidene]pentanoate (Compound 9) prepared in Example 7 and dimethyl (4S)-4-methyl-2-oxooctanyl phosphonate and isolated by means of silica gel column chromatography (hexane:ethyl acetate= 1:2) as an isomer having a polarity lower than the above-identified compound in Example 10, to obtain 30 mg of the above-identified compound.

$^1$H-NMR (CDCl$_3$) δ (ppm): 0.8–2.7 (m, 25H), 3.68 (s, 3H), 3.9–4.0 (m, 1H), 4.1–4.2 (m, 1H), 4.8–4.9 (m, 2H), 5.6–5.7 (m, 2H).

¹⁹F-NMR (CDCl₃, ppm): −84 (dd, J=254 Hz), −116 (d, J=254 Hz)

EXAMPLE 23

Preparation of sodium 5-[(1S,5R,6R,7R)-2-oxa-4,4-difluoro-7-hydroxy-6-{(3R,5S)-3-hydroxy-5-methyl-E-1-nonenyl}bicyclo3.3.0]octan-3-ylidene]pentanoate (Compound 23)

The above-identified compound was prepared by the same method as in Example 11 using methyl 5-[(1S,5R,6R,7R)-2-oxa-4,4-difluoro-7-hydroxy-6-{(3R,5S)-3-hydroxy-5-methyl-E-1-nonenyl}bicyclo[3.3.0]octan-3-ylidene]pentanoate (Compound 22) prepared in Example 22.

¹H-NMR (D₂O) δ (ppm): 0.8–2.8 (m, 25H), 3.9–4.2 (m, 2H), 4.5–5.0 (m, 2H), 5.5–5.6 (m, 2H).

¹⁹F-NMR (D₂O, ppm): −84 (dd, J=17, 248 Hz), −117 (d, J=248 Hz)

EXAMPLE 24

Preparation of methyl 5-[(1S,5R,6R,7R)-2-oxa-4,4-difluoro-7-hydroxy-6-{(3R,4RS)-3-hydroxy-4-methyl-E-1-nonen-6-ynyl}bicyclo[3.3.0]octan-3-ylidene]pentanoate (Compound 24)

The above-identified compound was prepared by the same method as in Example 10 using methyl 5-[(1S,5R,6R,7R)-2-oxa-4,4-difluoro-7-(2-tetrahydropyranyloxy)-6-hydroxymethyl-bicyclo[3.3.0]octan-3-ylidene]pentanoate (Compound 9) prepared in Example 7 and dimethyl (3RS)-3-methyl-2-oxo-5-octynyl phosphonate and isolated by means of silica gel column chromatography (hexane:ethyl acetate=1:2) as an isomer having a polarity lower than the above-identified compound in Example 14.

¹H-NMR (CDCl₃) δ (ppm): 0.9–2.8 (m, 21H), 3.68 (s, 3H), 3.9–4.3 (m, 2H), 4.8–4.9 (m, 2H), 5.6–5.8 (m, 2H).

¹⁹F-NMR (CDCl₃, ppm): −83—84 (m), −116—117 (m).

EXAMPLE 25

Preparation of sodium 5-[(1S,5R,6R,7R)-2-oxa-4,4-difluoro-7-hydroxy-6-{(3R,4RS)-3-hydroxy-4-methyl-E-1-none-6-ynyl}bicyclo[3.3.0]octan-3-ylidene] pentanoate (Compound 25)

The above-identified compound was prepared by the same method as in Example 11 using methyl 5-[(1S,5R,6R,7R)-2-oxa-4,4-difluoro-7-hydroxy-6-{(3R,4RS)-3-hydroxy-4-methyl-E-1-nonen-6-ynyl}bicyclo[3.3.0]octan-3-ylidene] pentanoate (Compound 24) prepared in Example 24.

¹H-NMR (D₂O) δ (ppm): 0.8–2.9 (m, 2H), 3.9–4.1 (m, 2H), 4.5–5.0 (m, 2H), 5.5–5.6 (m, 2H)

¹⁹F-NMR (D₂O, ppm): −83—84 (m), −116—117 (m).

EXAMPLE 26

Preparation of methyl 5-[(1S,5R,6R,7R)-2-oxa-4,4-difluoro-7-hydroxy-6-{(3R,4S)-3-hydroxy-4-methyl-E-1-nonen-6ynyl}bicyclo[3.3.0]octan-3-ylidene] pentanoate (Compound 26)

The above-identified compound was prepared by the same method as in Example 10 using methyl 5-[(1S,5R,6R,7R)-2-oxa-4,4-difluoro-7-(2-tetrahydropyranyloxy)-6-hydroxymethyl-bicyclo[3.3.0]octan-3-ylidene]pentanoate (Compound 9) prepared 9 in Example 7 and dimethyl (3S)-3-methyl-2-oxo-5-octynyl phosphonate and isolated by means of silica gel column chromatography (hexane:ethyl acetate=1:2) as an isomer having a polarity lower than the above-identified compound in Example 16.

¹H-NMR (CDCl₃) δ (ppm): 1.0–2.7 (m, 21H), 3.68 (s, 3H), 3.9–4.3 (m, 2H), 4.8–4.9 (m, 2H), 5.6 (m, 2H)

¹⁹F-NMR (CDCl₃, ppm): −84 (dd, J=17, 254 Hz), −116 (d, J=254 Hz).

EXAMPLE 27

Preparation of sodium 5-[(1S,5R,6R,7R)-2-oxa-4,4-difluoro-7-hydroxy-6-}(3R,4S)-3-hydroxy-4-methyl-E-1-nonen-6-ynyl}bicyclo[3.3.0]octan-3-ylidene] pentanoate (Compound 27)

The above-identified compound was prepared by the same method as in Example 11 using methyl 5-[(1S,5R,6R,7R)-2-oxa-4,4-difluoro-7-hydroxy-6-{(3R,4S)-3-hydroxy-4-methyl-E-1-nonen-6-ynyl}bicyclo[3.3.0]octan-3-ylidene]pentanoate (Compound 26) prepared in Example 26.

¹H-NMR (D₂O) δ (ppm): 0.8–2.9 (m, 2H), 3.9–4.1 (m, 2H), 4.5–5.0 (m, 2H), 5.5–5.6 (m, 2H)

¹⁹F-NMR (D₂O, ppm): −84 (dd, J=17, 248 Hz), −117 (d, J=248 Hz)

EXAMPLE 28

Preparation of methyl 5-[(1S,5R,6R,7R)-2-oxa-4,4-difluoro-7-hydroxy-6-{(3R)-3-hydroxy-4-(3-methylphenyl)-E-1-butenyl}bicyclo[3.3.0]octan-3-ylidene]pentanoate (Compound 28)

The above-identified compound was prepared in the same manner as in Example 10 using methyl 5-[(1S,5R,6R,7R)-2-oxa-4,4-difluoro-7-(2-tetrahydropyranyloxy)-6-hydroxymethyl-bicyclo[3.3.0]octan-3-ylidene]pentanoate (Compound 9) prepared in Example 7 and dimethyl 2-oxo-3-(2-methylphenyl)propyl phosphonate and isolated by means of silica gel column chromatography (methylene chloride:acetone=2:1) as an isomer having a polarity lower than the above-identified compound in Example 20.

¹H-NMR (CDCl₃) δ (ppm): 1.7–2.9 (m, 12H), 2.32 (m, 3H), 3.66 (S, 3H), 3.80 (m, 1H), 4.33 (m, 1H), 4.7–4.9 (m, 2H), 5.4–5.8 (m, 2H), 7.0–7.2 (m, 4H)

¹⁹F-NMR (CDCl₃, ppm): −84 (dd, J=12, 253 Hz), −116 (d, J=253 Hz)

EXAMPLE 29

Preparation of sodium 5-[(1S,5R,6R,7R)-2-oxa-4,4-difluoro-7-hydroxy-6-{(3R)-3-hydroxy-4-(3-methylphenyl)-E-1-butenyl}bicyclo[3.3.0]octan-3-ylidene]pentanoate (Compound 29)

The above-identified compound was prepared by the same method as in Example 11 using methyl 5-[(1S,5R,6R,7R)-2-oxa-4,4-difluoro-7-hydroxy-6-{(3R)-3-hydroxy-4-(3-methylphenyl)-E-1-butenyl}bicyclo[3.3.0]octan-3-ylidene] pentanoate (Compound 28) prepared in Example 28.

¹H-NMR (D₂O) δ (ppm): 1.6–3.0 (m, 15H), 3.8–4.4 (m, 2H), 4.7–4.9 (m, 2H), 5.4–5.8 (m, 2H), 7.0–7.2 (m, 4H)

¹⁹F-NMR (D₂O, ppm): −84 (dd, J=12, 253 Hz), −116 (d, J=253 Hz)

EXAMPLE 30

Preparation of (1S,5R,6R,7R)-2-oxa-4-fluoro-7-t-butyldimethylsiloxy-6-{(3S,5S)-3-t-butyldimethylsiloxy-5-methyl-E-1-nonenyl}bicyclo[3.3.0]octan-3-one (Compound 33)

To a THF (1 ml) solution of hexamethyldisilazane (51 μl, 0.242 mmol), 0.14 ml of n-butyl lithium (1.56M, hexane solution) was added at −78° C., followed by stirring for 30 minutes to obtain a lithium hexamethyldisilazide solution. To this solution, a THF solution (2 ml) of 105 mg of (1S,5R,6R,7R)-2-oxa-7-t-butyldimethylsiloxy-6-{(3S,5S)-3-t-butyldimethylsiloxy-5-methyl-E-1-nonenyl}bicyclo[3.3.0]octan-3-one (Compound 32) was dropwise added at −78° C., and the mixture was stirred for 30 minutes. Then, 76.2 mg of N-fluorobenzenesulfonimide was added thereto at −78° C. The mixture was stirred at −78° C. for 15 minutes, at 0° C. for 30 minutes and at room temperature for 30 minutes and then poured into a saturated ammonium chloride aqueous solution, and the mixture was extracted with ethyl acetate. The extract was purified by silica gel column chromatography (ethyl acetate:hexane=1:30 to 1:10) to obtain 40 mg of the above-identified compound.

$^1$H-NMR (CDCl$_3$) δ (ppm): 0.04 (m, 12H), 0.86 (m, 24H), 1.0–4.2 (m, 15H), 4.9–5.7 (m, 4H).

$^{19}$F-NMR (CDCl$_3$, ppm): −177 (dd, J=30.2, 52.7 Hz), −203 (d, J=48.8 Hz).

Mass spectrum: 542 (M$^+$)

EXAMPLE 31

Preparation of (1S,5R,6R,7R)-2-oxa-4,4-difluoro-7-t-butyldimethylsiloxy-6-{(3S,5S)-3-t-butyldimethylsiloxy-5-methyl-E-1-nonenyl}bicyclo[3.3.0]octan-3-one (Compound 34)

To a THF (14 ml) solution of diisopropylamine (1.23 ml, 0.9 mmol), 4.88 ml of n-butyl lithium (1.66M, hexane solution) was added at −78° C., followed by stirring for 30 minutes to obtain a lithium diisopropylamide solution. In a separate container, 1.47 g (10.8 mmol) of anhydrous zinc chloride was taken, and a THF solution (20 ml) of 3.57 g (6.76 mmol) of (1S,5R,6R,7R)-2-oxa-4-fluoro-7-t-butyldimethylsiloxy-6-{(3S)-3-t-butyldimethylsiloxy-5-methyl-E-1-nonenyl}bicyclo[3.3.0]octan-3-one (Compound 33) prepared in Example 30 was added thereto. This solution was cooled to −78° C. and the above-mentioned lithium diisopropylamide solution was dropwise added thereto at −78° C. The mixture was stirred for 20 minutes. Then, 2.56 g (8.1 mmol) of N-fluorobenzenesulfonimide was added thereto at −78° C. The mixture was stirred at −78° C. for 30 minutes and at room temperature for 30 minutes, and then poured into a saturated sodium hydrogen carbonate aqueous solution. The mixture was extracted with ethyl acetate. The extract was purified by silica gel column chromatography (ethyl acetate:hexane=1:30 to 1:10) to obtain 2.90 g of the above-identified compound.

$^1$H-NMR (CDCl$_3$) δ (ppm): 0.04 (m, 12H), 0.84–0.88 (m, 24H), 1.0–1.5 (m, 9H), 2.1–2.2 (m, 2H), 2.9–3.1 (m, 2H), 4.0–4.2 (m, 2H), 5.15 (m, 1H), 5.36 (dd, J=7.7, 15.3 Hz, 1H), 5.54 (dd, J=6.3, 15.3 Hz, 1H).

$^{19}$F-NMR (CDCl$_3$, ppm): −92 (dd, J=26, 282 Hz), −114 (d, J=282 Hz).

Mass spectrum: 560 (M$^+$)

EXAMPLE 32

Preparation of (1S,5R,6R,7R)-2-oxa-4,4-difluoro-7-t-butyldimethylsiloxy-6-{(3S,5S)-3-t-butyldimethylsiloxy-5-methyl-E-1-nonenyl}bicyclo[3.3.0]octan-3-one (Compound 34)

513 mg of the above-identified compound was obtained in the same manner as in Example 3 using 854 mg (1.62 mmol) of (1S,5R,6R,7R)-2-oxa-7-t-butyldimethylsiloxy-6-{(3S,5S)-3-t-butyldimethylsiloxy-5-methyl-E-1-nonenyl}bicyclo[3.3.0]octan-3-one (Compound 32).

$^1$H-NMR (CDCl$_3$) δ (ppm): 0.04 (m, 12H), 0.84–0.88 (m, 24H), 1.0–1.5 (m,9H), 2.1–2.2 (m, 2H), 2.9–3.1 (m, 2H), 4.0–4.2 (m, 2H), 5.15 (m, 1H), 5.36 (dd, J=7.7, 15.3 Hz, 1H), 5.54 (dd, J=6.3, 15.3 Hz, 1H).

$^{19}$F-NMR (CDCl$_3$, ppm): −92 (dd, J=26, 282 Hz), −114 (d, J=282 Hz).

EXAMPLE 33

Preparation of (1S,5R,6R,7R)-2-oxa-3-{4-(4-methyl-2,6,7-trioxabicyclo[2.2.2]octanyl)butylidene}-4,4-difluoro-7-t-butyldimethylsiloxy-6-{(3S,5S)-3-t-butyldimethylsiloxy-5-methyl-E-1-nonenyl}bicyclo[3.3.0]octane (Compound 35)

A dry ethyl ether (30 ml) solution of 1.13 g of 1-(4-iodobutyl)-4-methyl-2,6,7-trioxabicyclo[2.2.2]octane (Compound 4) was cooled to −78° C., and 5.07 ml of t-butyl lithium (1.48M, pentane solution) was added thereto. The mixture was stirred at −78° C. for two hours. To this solution, an ethyl ether solution (10 ml) of 1.75 g of (1S,5R,6R,7R)-2-oxa-4,4-difluoro-7-t-butyldimethylsiloxy-6-{(3S,5S)-3-t-butyldimethylsiloxy-5-methyl-E-1-nonenyl}bicyclo[3.3.0]octan-3-one (Compound 34) was added at −78° C. The mixture was stirred −78° C. for one hour and at −60° C. for one hour. The mixture was poured into a sodium hydrogen carbonate aqueous solution, and the mixture was extracted with ethyl acetate. The extract solution was washed with a saturated sodium chloride aqueous solution and then concentrated under reduced pressure. To the residue, 10 ml of methylene chloride was added, and 2.6 ml of triethylamine and 0.72 ml of methanesulfonyl chloride were added at 0° C. Then, the mixture was stirred at room temperature for 1.5 hours. The mixture was poured into a sodium hydrogen carbonate aqueous solution, and the mixture was extracted with ethyl acetate. The extract solution was concentrated under reduced pressure and then purified by silica gel column chromatography (ethyl acetate:hexane=1:30 to 1:10) to obtain 1.83 g of the above-identified compound.

$^1$H-NMR (CDCl$_3$) δ (ppm): 0.02–0.05 (m, 12H), 0.80–0.89 (m, 27H), 1.2–2.5 (m, 19H), 3.84 (m, 1H), 3.88 (s, 6H), 4.13 (m, 1H), 4.7–4.9 (m, 2H), 5.53 (m, 2H).

$^{19}$F-NMR (CDCl$_3$, ppm): −83 (d, J=251 Hz), −115 (d, J=250 Hz).

EXAMPLE 34

Preparation of methyl 5-[(1S,5R,6R,7R)-2-oxa-4,4-difluoro-7-t-butyldimethylsiloxy-6-{(3S,5S)-3-t-butyldimethylsiloxy-5-methyl-E-1-nonenyl}bicyclo[3.3.0]octan-3-ylidene]pentanoate (Compound 36)

To a 1,2-dimethoxyethane (25 ml) solution of 1.83 g of (1S,5R,6R,7R)-2-oxa-3-{4-(4-methyl-2,6,7-trioxabicyclo[2.2.2]octanyl)butylidene}-4,4-difluoro-7-t-butyldimethylsiloxy-6-{(3S,5S)-3-t-butyldimethylsiloxy-5-methyl-E-1-nonenyl}bicyclo[3.3.0]octane (Compound 35) prepared in Example 33, 2.5 ml of a 10% sodium hydrogen sulfate aqueous solution was added at 0° C., and the mixture was stirred for 30 minutes. The mixture was poured into a sodium hydrogen carbonate aqueous solution, and the mixture was extracted with ethyl acetate. The extract solution was concentrated under reduced pressure. To the residue, 25 ml of methanol and 680 mg of potassium carbonate were added, and the mixture was stirred at room temperature for two hours. The mixture was poured into an aqueous sodium hydrogen carbonate solution, and the mixture was extracted with ethyl acetate-hexane (1:1). The extract solution was concentrated under reduced pressure and purified by silica gel column chromatography (ethyl acetate:hexane=1:30 to 1:10) to obtain 981 mg of the above-identified compound.

$^1$H-NMR (CDCl$_3$) δ (ppm): 0.03–0.11 (m, 12H), 0.85–0.89 (m, 24H), 1.1–2.6 (m, 19H), 3.67 (s, 3H), 3.8–4.2 (m, 2H), 4.7–4.9 (m, 2H), 5.4–5.6 (m, 2H).

$^{19}$F-NMR (CDCl$_3$, ppm): –83 (dd, J=14, 251 Hz), –115 (d, J=251 Hz).

Mass spectrum: 659 (M$^+$+1).

EXAMPLE 35

Preparation of methyl 5[(1S,5R,6R,7R)-2-oxa-4,4-difluoro-7-hydroxy-6-{(3S,5S)-3-hydroxy-5-methyl-E-1-nonenyl}bicyclo[3.3.0]octan-3-ylidene]pentanoate (Compound 10)

To a THF (15 ml) solution of 976 mg of methyl 5-[(1S,5R,6R,7R)-2-oxa-4,4-difluoro-7-t-butyldimethylsiloxy-6-{(3S,5S)-3-t-butyldimethylsiloxy-5-methyl-E-1-nonenyl}bicyclo[3.3.0]octan-3-ylidene]pentanoate (Compound 36) prepared in Example 34, 4.5 ml of tetrabutyl ammonium fluoride (1M, THF solution) was added, and the mixture was stirred at room temperature for 18 hours. The reaction solution was concentrated under reduced pressure and purified by silica gel column chromatography to obtain 470 mg of the above-identified compound.

$^1$H-NMR (CDCl$_3$) δ (ppm): 0.8–2.7 (m, 25H), 3.67 (s, 3H), 3.9–4.3 (m, 2H), 4.7–4.9 (m, 2H), 5.5–5.7 (m, 2H).

$^{19}$F-NMR (CDCl$_3$, ppm): –84 (dd, J=17, 248 Hz), –117 (d, J=248 Hz).

Mass spectrum: 431 (M$^+$+1).

EXAMPLE 36

Preparation of methyl 5-[(1S,5R,6R,7R)-2-oxa-4,4-difluoro-7-(2-tetrahydropyranyloxy)-6-[(3S,5S)-3-(2-tetrahydropyranyloxy)-5-methyl-E-1-nonenyl}bicyclo[3.3.0]octan-3-ylidene]pentanoate (Compound 39)

To a dry THF (2 ml) solution of 180 mg of (4-carboxybutyl)triphenyl phosphonium bromide, 0.81 ml of a 0M sodium hexamethyldisilazide (THF solution) was added, and the mixture was heated and refluxed for one hour. Then, a dry THF solution of 131 mg of (1S,5R,6R,7R)-2-oxa-4,4-difluoro-7-(2-tetrahydropyranyloxy)-6-{(3S,5S)-3-(2-tetrahydropyranyloxy)-5-methyl-E-1-nonenyl}bicyclo[3.3.0]octan-3-one (Compound 38) was added thereto at room temperature, and the mixture was stirred for 4 hours. The reaction solution was concentrated under reduced pressure, and an aqueous sodium hydrogen carbonate solution was added thereto. The mixture was extracted with ethyl acetate-hexane (1:1), and the extract solution was concentrated under reduced pressure. The residue was dissolved in benzene-methanol (4:1) (2.5 ml), and 1.3 ml of 10% trimethylsilyldiazomethane (hexane solution) was added thereto., The mixture was stirred at room temperature for 30 minutes. Acetic acid was added thereto until nitrogen was no more generated. The mixture was concentrated under reduced pressure and purified by silica gel column chromatography (ethyl acetate-hexane=1:7) to obtain 87 mg of the above-identified compound.

$^1$H-NMR (CDCl$_3$) δ (ppm): 0.8–2.8 (m, 37H), 3.4–3.5 (m, 2H), 3.67 (s, 3H), 3.8–4.3 (m, 4H), 4.6–4.9 (m, 4H), 5.3–5.7 (m, 2H).

$^{19}$F-NMR (CDCl$_3$, ppm): –83—84 (m), –115—117 (m).

Using the same materials as above, the above-identified compound was prepared by changing the base. The base, the type of the base used and the yield of the above-identified compound are shown in Table 2.

TABLE 2

| No. | Base | Yield (%) |
|---|---|---|
| 1 | NaN(SiMe$_3$)$_2$ | 57 |
| 2 | NaNH$_2$, (Me$_3$Si)$_2$NH | 46 |
| 3 | n-BuLi | 30 |
| 4 | t-BuOK | 36 |
| 5 | KN(SiMe$_3$)$_2$ | 56 |

EXAMPLE 37

Preparation of methyl 5-[(1S,5R,6R,7R)-2-oxa-4,4-difluoro-7-(2-tetrahydropyranyloxy)-6-(t-butyldimethylsiloxy)methyl-bicyclo[3.3.0]octan-3-ylidene] pentanoate (Compound 8)

The above-identified compound was prepared in the same manner as in Example 36 using (1S,5R,6R,7R)-2-oxa-4,4-difluoro-7-(2-tetrahydropyranyloxy)-6-(t-butyldimethylsiloxy)methyl-bicyclo[3.3.0]octan-3-one (Compound 3).

$^1$H-NMR (CDCl$_3$) δ (ppm): 0.06 (m, 6H), 0.89 (m, 9H), 1.2–2.7 (m, 15H), 3.09 (m, 1H), 3.4–3.9 (m, 4H), 3.69 (s, 3H), 4.1 (m, 1H), 4.64 (m, 1H), 4.7–4.8 (m, 2H).

$^{19}$F-NMR (CDCl$_3$, ppm): –84 (m), –117 (m)

EXAMPLE 38

Preparation of methyl 5-[(1S,5R,6R,7R)-2-oxa-4,4-difluoro-7-hydroxy-6-{(3S)-3-hydroxy-1-octynyl}bicyclo[3.3.0]octan-3-ylidene]pentanoate (Compound 30)

Step 1

Preparation of (1S,5R,6R,7R)-2-oxa-4-fluoro-7-t-butyldimethylsiloxy-6-{(3S)-3-t-butyldimethylsiloxy-1-octynyl}-bicyclo[3.3.0]octan-3-one (1S,5R,6R,7R)-2-oxa-7-hydroxy-6-{(3S)-3-hydroxy-1-octynyl}-bicyclo[3.3.0]octan-3-one prepared by the method of Fried et al. (Tetrahedron Letters, 3899 (1973)) was silylated by means of imidazole and t-butyldimethylsilyl chloride in dimethylformamide to obtain (1S,5R,6R,7R)-2-oxa-7-t-butyldimethylsiloxy-6-{(3S)-3-t-butyldimethylsiloxy-1-octynyl{-bicyclo[3.3.0]octan-3-one.

To a THF (8 ml) solution of hexamethyldisilazane (615 μl), 1.66 ml of n-butyl lithium (1.56M, hexane solution) was added at –78° C., followed by stirring for 30 minutes to obtain a lithium hexamethyldisilazide solution. To this solution, a THF solution (10 ml) of 1.21 g of (1S,5R,6R,7R)-2-oxa-7-t-butyldimethylsiloxy-6-{(3S)-3-t-butyldimethylsiloxy-1-octynyl}-bicyclo[3.3.0]octan-3-one was dropwise added at −78° C., and the mixture was stirred for 30 minutes. Then, 930 mg of N-fluorobenzenesulfonimide was added thereto at −78° C. The mixture was stirred at −78° C. for 15 minutes, at 0° C. for 30 minutes and at room temperature for 30 minutes, and then poured into a saturated ammonium chloride aqueous solution. The mixture was extracted with ethyl acetate. The extract was purified by silica gel column chromatography (ethyl acetate:hexane=1:30 to 1:10) to obtain 643 mg of the above-identified compound.

$^1$H-NMR (CDCl$_3$) δ (ppm): 0.04 (m, 12H), 0.88 (m, 21H), 1.0–5.4 (m, 16H).

$^{19}$F-NMR (CDCl$_3$, ppm): −178 (dd, 30.1, 52.9 Hz).

Step 2

Preparation of (1S,5R,6R,7R)-2-oxa-4,4-difluoro-7-t-butyldimethylsiloxy-6-{(3S)-3-t-butyldimethylsiloxy-1-octynyl}-bicyclo[3.3.0]octan-3-one To a THF (2 ml) solution of diisopropylamine (0.18 ml), 0.74 ml of n-butyl lithium (1.66M, hexane solution) was added at −78° C., followed by stirring for 30 minutes to obtain a lithium diisopropylamide solution. In a separate container, 0.23 g of anhydrous zinc chloride was taken, and a THF solution (3 ml) of 0.54 g (1S,5R,6R,7R)-2-oxa-4-fluoro-7-t-butyldimethylsiloxy-6-{(3S)-3-t-butyldimethylsiloxy-1-octynyl}-bicyclo[3.3.0]octan-3-one prepared in step 1 was added thereto. This solution was cooled to −78° C., and the above lithium diisopropylamide solution was dropwise added thereto at −78° C. The mixture was stirred for 20 minutes. Then, 0.38 g of N-fluorobenzenesulfonimide was added thereto at −78° C. The mixture was stirred at −78° C. for 60 minutes and at room temperature for 30 minutes. Then, the mixture was poured into a saturated sodium hydrogen carbonate aqueous solution, and the mixture was extracted with ethyl acetate. The extract was purified by silica gel column chromatography (ethyl acetate:hexane=1:30 to 1:10) to obtain 0.43 g of the above-identified compound.

$^1$H-NMR (CDCl$_3$) δ (ppm): 0.04 (m, 12H), 0.89 (m, 21H), 1.0–5.4 (m, 15H).

$^{19}$F-NMR (CDCl$_3$, ppm): −92 (dd, J=25, 280 Hz), −113 (d, J=280 Hz).

Step 3

Preparation of methyl 5-[(1S,5R,6R,7R)-2-oxa-4,4-difluoro-7-t-butyldimethylsiloxy-6-}(3S)-3-t-butyldimethylsiloxy-1-octynyl}-bicyclo[3.3.0]octan-3-ylidene]pentanoate A dry ethyl ether (8 ml) solution of 0.29 g of 1-(4-iodobutyl)-4-methyl-2,6,7-trioxabicyclo[2.2.2]octane (Compound 4) was cooled to −78° C., and 1.4 ml of t-butyl lithium (1.48M, pentane solution) was added thereto. The mixture was stirred at −78° C. for two hours. To this mixture, a THF solution (3 ml) of 0.44 g of (1S,5R,6R,7R)-2-oxa-4,4-difluoro-7-t-butyldimethylsiloxy-6-{(3S)-3-t-butyldimethylsiloxy-1-octynyl}-bicyclo[3.3.0]octan-3-one prepared in step 2 was added. Then, the mixture was stirred at −78° C. for one hour and at −60° C. for one hour, and then poured into an aqueous sodium carbonate solution. The mixture was extracted with ethyl acetate. The extract solution was washed with a saturated sodium chloride aqueous solution and then concentrated under reduced pressure.

To the residue, 3 ml of methylene chloride was added, and 0.79 ml of triethylamine and 0.21 ml of methanesulfonyl chloride were added at 0° C. Then, the mixture was stirred at room temperature for 1.5 hours and then poured into an aqueous sodium hydrogen carbonate solution. The mixture was extracted with ethyl acetate. The extract solution was concentrated under reduced pressure and purified by silica gel column chromatography (ethyl acetate:hexane=1:30 to 1:10) to obtain 0.39 mg of (1S,5R,6R,7R)-2-oxa-{4-(4-methyl-2,6,7-trioxabicyclo[2.2.2]octanyl)butylidene}-4,4-difluoro-7-t-butyldimethylsiloxy-6-{(3S)-3-t-butyldimethylsiloxy-1-octynyl}bicyclo[3.3.0]octane. To a dimethoxyethane (5 ml) solution thereof, 0.5 ml of a 10% sodium hydrogen sulfate aqueous solution was added at 0° C., and the mixture was stirred for 30 minutes. The mixture was poured into an aqueous sodium hydrogen carbonate solution, and the mixture was extracted with ethyl acetate. The extract solution was concentrated under reduced pressure. To the residue, 5 ml of methanol and 0.19 g of potassium carbonate were added. The mixture was stirred at room temperature for two hours. The mixture was poured into an aqueous sodium hydrogen carbonate solution, and the mixture was extracted with ethyl acetate-hexane (1:1). The extract solution was concentrated under reduced pressure and purified by silica gel column chromatography (ethyl acetate:hexane=1:30 to 1:10) to obtain 0.29 g of the above-identified compound.

$^1$H-NMR (CDCl$_3$) δ (ppm): 0.03–0.11 (m, 12H), 0.84–0.95 (m, 18H), 1.1–2.6 (m, 21H), 3.67 (s, 3H), 3.8–5.0 (m, 4H).

$^{19}$F-NMR (CDCl$_3$, ppm): −83 (dd, J=17, 249 Hz), −115 (d, J=249 Hz).

Step 4

Preparation of methyl 5-[(1S,5R,6R,7R)-2-oxa-4,4-difluoro-7-hydroxy-6-{(3S)-3-hydroxy-1-octynyl}bicyclo[3.3.0]octan-3-ylidene]pentanoate (Compound 30)

To a THF (5 ml) solution of 284 mg of methyl 5-[(1S,5R,6R,7R)-2-oxa-4,4-difluoro-7-t-butyldimethylsiloxy-6-{(3S)-3-t-butyldimethylsiloxy-1-octynyl}bicyclo[3.3.0]octan-3-ylidene]pentanoate, 1.5 ml of tetrabutyl ammonium fluoride (1M, THF solution) was added, and the mixture was stirred at room temperature for 18 hours. The reaction solution was concentrated under reduced pressure and purified by silica gel column chromatography (acetone-methylene chloride) to obtain 140 mg of the above-identified compound.

$^1$H-NMR (CDCl$_3$) δ (ppm): 0.9–3.0 (m, 21H), 3.66 (s, 3H), 3.8–5.0 (m, 4H).

$^{19}$F-NMR (CDCl$_3$, ppm): −84 (dd, J=17, 248 Hz), −116 (d, J=248 Hz).

EXAMPLE 39

Preparation of sodium 5-[(1S,5R,6R,7R)-2-oxa-4,4-difluoro-7-hydroxy-6-{(3S)-3-hydroxy-1-octynyl}bicyclo[3.3.0]octan-3-ylidene]pentanoate (Compound 31)

The above-identified compound was prepared by the same method as in Example 11 using methyl 5-[(1S,5R,6R,7R)-2-oxa-4,4-difluoro-7-hydroxy-6-{(3S)-3-hydroxy-1-octynyl}bicyclo[3.3.0]octan-3-ylidene]pentanoate (Compound 30) prepared in Example 38.

$^1$H-NMR (D$_2$O) δ (ppm): 0.9–3.0 (m, 21H), 3.7–5.0 (m, 4H).

$^{19}$F-NMR (D$_2$O, ppm): −84 (dd, J=17, 250 Hz), −116 (d, J=250 Hz).

EXAMPLE 40

Platelet aggregation inhibitory activities in vitro

Platelet aggregation inhibitory activities of test compounds in vitro were measured by using human platelets.

Into a plastic container containing one volume of a 3.8% sodium citrate solution, 9 volumes of blood of a healthy person was collected, and the container was gently turned over for admixing. The mixture was centrifugally separated at 1,000 rpm for 10 minutes at room temperature, whereupon the supernatant was taken as a platelet-rich plasma (PRP). The lower layer was further centrifugally separated at 3,000 rpm for 15 minutes at room temperature, whereupon the supernatant was taken as a platelet-poor plasma (PPP). PRP was diluted with PPP so that the number of platelets became about 30×10$^4$/μl. An aggregometer was calibrated, and then 200 μl of PRP thus prepared was heated at 37° C. for one minute. Then, 25 μl of a solution obtained by diluting a test compound with a physiological sodium chloride solution, was added thereto, and the mixture was heated at 37° C. for one minute. Then, 25 ml of an adenosine-5'-1.5 sodium diphosphate (ADP, Sigma) solution was added thereto so that the final concentration would be 4 μM, whereby the change in transmittance was recorded by the aggregometer. The transmittance was measured with respect to the solution immediately after dissolving the test compound in the physiological sodium chloride solution and the solution after leaving it at 25° C. for 24 hours. The solution of the test compound was dissolved in a physiological sodium chloride solution and then used by diluting it with a physiological sodium chloride solution. IC$_{50}$ (50% inhibitory concentration) was shown in Table 3.

Aggregation inhibition (%)=(1−T/T$_0$)×100

T$_0$: Transmittance in the case where the physiological sodium chloride solution was added.

T: Transmittance in the case where the test compound was added.

As shown in Table 3, it has been confirmed that the compounds of the present invention exhibit excellent platelet aggregation inhibitory activities, and yet they are remarkably stabilized compounds with the platelet aggregation inhibitory activities which do not deteriorate even after 24 hours. Further, in particular, Compounds 11 and 27 of the present invention have activities close to natural type prostacyclin, and Compounds 15 and 17 of the present invention have even higher activities than natural type prostacyclin. Compound 31 has low activities as compared with other compounds (11, 13, 15, 17, 19, 21, 23, 25 and 27).

Compound 31 is 7,7-difluoro-13,14-dehydroprostacyclin disclosed in Japanese International Patent Publication No. 501319/1981, which was synthesized anew by the process developed by the present inventors as described in Examples 38 and 39. Further, PGI$_2$Na represents a sodium salt of natural type prostacyclin.

TABLE 3

| Test compound | IC$_{50}$ (ng/ml) | |
|---|---|---|
| | Immediately after preparation | 24 hours later |
| Compound 11 | 8.6 | 7.8 |
| Compound 13 | 66.3 | 62.9 |
| Compound 15 | 0.79 | 0.78 |
| Compound 17 | 0.38 | 0.39 |
| Compound 19 | 56.1 | 60.4 |
| Compound 21 | 8.7 | 8.9 |
| Compound 23 | 59.0 | 58.2 |
| Compound 25 | 27.0 | 28.1 |
| Compound 27 | 8.4 | 8.0 |
| Compound 29 | >200 | >200 |
| Compound 31 | 73.7 | 75.8 |
| PGI$_2$Na | 2.1 | >200 |

EXAMPLE 41

Stability test in an aqueous solution

A test compound was dissolved in ethanol to a concentration of 1 mg/ml. Then, it was diluted with a physiological sodium chloride solution to obtain a solution having a concentration of 10 μg/ml. The solution was stored at 25° C., and the remaining ratio of the test compound was measured as time passed. The remaining ratio was quantitatively analyzed by an internal standard (methyl benzoate) method using high performance liquid chromatography (Shimadzu LC9A, SPC-6AU; Milipore 805-DS). The column used was YMC AM312 (ODS), and the eluent used was a solvent mixture of acetonitrile and a 1% triethylamine-phosphoric acid buffer solution (pH6.3).

In Table 4, the remaining ratio and the half-life were shown. As shown in Table 4, it has been confirmed that the compounds of the present invention exhibit excellent stability in their aqueous solutions.

TABLE 4

| Test compound | Remaining ratio | | Half-life |
|---|---|---|---|
| | 7 days | 20 days | (days) |
| Compound 11 | 102.2 | 96.8 | >90 |
| Compound 13 | 100.4 | 98.0 | >90 |
| Compound 15 | 98.9 | 97.8 | >90 |
| Compound 17 | 101.5 | 100.1 | >90 |
| Compound 19 | 99.3 | 97.2 | >90 |
| Compound 21 | 101.2 | 100.5 | >90 |
| Compound 23 | 100.5 | 100.1 | >90 |
| Compound 25 | 101.0 | 99.8 | >90 |
| Compound 27 | 99.5 | 100.2 | >90 |
| Compound 29 | 99.1 | 99.3 | >90 |
| Compound 31 | 99.5 | 97.0 | >90 |

What is claimed is:

1. A difluorolactone of the following formula (I):

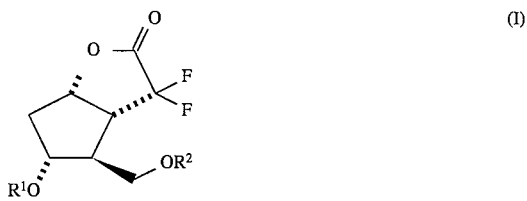

wherein each of R$^1$ and R$^2$ which are independent of each other, is a hydrogen atom or a protecting group for a hydroxyl group.

2. A process for producing a compound of the following formula (XV), which comprises introducing an α-chain moiety to a compound of the following formula (XII):

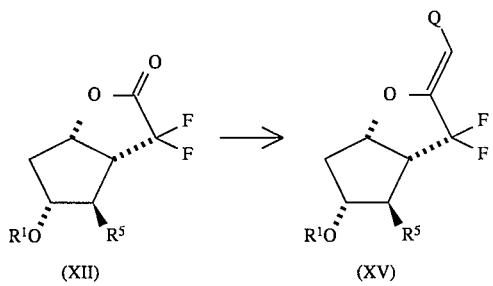

wherein Q is a substituted or unsubstituted $C_{1-10}$ alkyl group, a substituted or unsubstituted $C_{1-10}$ alkenyl group, a substituted or unsubstituted $C_{1-10}$ alkynyl group, a substituted or unsubstituted $C_{3-8}$ cycloalkyl group, a substituted or unsubstituted aralkyl group, or a substituted or unsubstituted aryl group, $R^1$ is a hydrogen atom or a protecting group for a hydroxyl group, $R^5$ is —$CH_2OR^2$ or —A—$CH(OR^3)$—R, wherein A is an ethylene group, a vinylene group, or an ethynylene group, R is a substituted or unsubstituted $C_{1-10}$ alkyl group, a substituted or unsubstituted $C_{1-10}$ alkenyl group, a substituted or unsubstituted $C_{1-10}$ alkynyl group, a substituted or unsubstituted $C_{3-8}$ cycloalkyl group, a substituted or unsubstituted aralkyl group, or a substituted or unsubstituted aryloxy group, and each of $R^2$ and $R^3$ which are independent of each other, is a hydrogen atom or a protecting group for a hydroxyl group.

3. The process according to claim 2, wherein Q is a monovalent organic group of the formula -B-Z (wherein B is a lower alkylene group, a lower cycloalkylene group, a lower alkylene group containing a lower cycloalkylene group, a lower alkylene group containing an ether bond or a thioether bond, or a phenylene group, and Z is a carboxyl group, a formyl group, a hydroxyl group, or a group which can be converted to such a polar group), $R^5$ is —$CH_2OR^2$, and each of $R^1$ and $R^2$ is a protecting group for a hydroxyl group.

4. The process according to claim 2, wherein the introduction of the α-chain moiety is carried out by an addition reaction of an organometallic compound of the following formula (VIII), followed by a dehydration reaction:

wherein M is a metal atom, L is a ligand to the metal, m is an integer of from 1 to 8, and n is an integer of from 0 to 10.

5. The process according to claim 2, wherein the introduction of the α-chain moiety is carried out by reacting a phosphorane of the following formula (XVI):

$$Q\text{—}CH=P(R^7)_3 \quad \quad (XVI)$$

wherein $R^7$ is a monovalent organic group.

6. A process for producing a compound of the following formula (XIV) having a ω-chain moiety introduced, which comprises introducing the ω-chain moiety to a compound of the following formula (XIII):

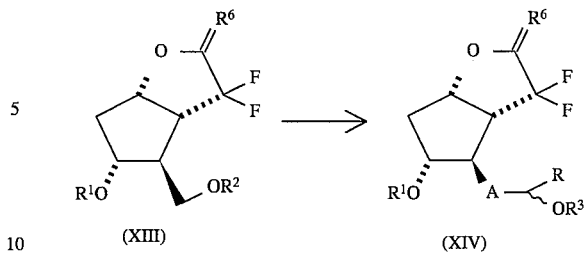

wherein A is an ethylene group, a vinylene group, or an ethynylene group, R is a substituted or unsubstituted $C_{1-10}$ alkyl group, a substituted or unsubstituted $C_{1-10}$ alkenyl group, a substituted or unsubstituted $C_{1-10}$ alkynyl group, a substituted or unsubstituted $C_{3-8}$ cycloalkyl group, a substituted or unsubstituted aralkyl group, or a substituted or unsubstituted aryloxy group, each of $R^1$, $R^2$ and $R^3$ which are independent of one another, is a hydrogen atom or a protecting group for a hydroxyl group, and $R^6$ is an oxygen atom of the formula =O, or a bivalent organic group of the formula =CH—Q, wherein Q is a substituted or unsubstituted $C_{1-10}$ alkyl group, a substituted or unsubstituted $C_{1-10}$ alkenyl group, a substituted or unsubstituted $C_{1-10}$ alkynyl group, a substituted or unsubstituted $C_{3-8}$ cycloalkyl group, a substituted or unsubstituted aralkyl group, or a substituted or unsubstituted aryl group.

7. The process according to claim 6, wherein R is a $C_{4-10}$ branched alkyl group, a $C_{4-10}$ alkenyl group, a $C_{4-10}$ alkynyl group, or a $C_{1-2}$ alkyl group having a tolyl group, each of $R^1$ and $R^3$ is a protecting group for a hydroxyl group, $R^2$ is a hydrogen atom, and $R^6$ is an oxygen atom of the formula =O.

8. The process according to claim 6, wherein R is a $C_{4-10}$ branched alkyl group, a $C_{4-10}$ alkenyl group, a $C_{4-10}$ alkynyl group, or a $C_{1-2}$ alkyl group having a tolyl group, each of $R^1$ and $R^2$ is a protecting group for a hydroxyl group, $R^2$ is a hydrogen atom, and $R^6$ is a bivalent organic group of the formula =CH—Q, wherein Q is a monovalent organic group of the formula -B-Z (wherein B is a lower alkylene group, a lower cycloalkylene group, a lower alkylene group containing a lower cycloalkylene group, a lower alkylene group containing an ether bond or a thioether bond, or a phenylene group, and Z is a carboxyl group, a formyl group, a hydroxyl group, or a group which can be converted to such a polar group).

9. The process according to claim 6, wherein the introduction of the ω-chain moiety is carried out by converting —$CH_2OR^2$ to —CHO, and then reacting the product with an organic phosphonate of the following formula (IX), followed by reduction:

wherein $R^4$ is a lower alkyl group.

10. A process for producing a compound of the following formula (XII), which comprises fluorinating a compound of the following formula (XI):

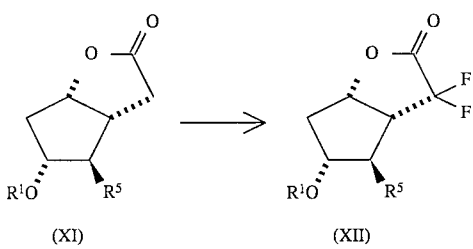

wherein $R^1$ is a hydrogen atom or a protecting group for a hydroxyl group, and $R^5$ is —$CH_2OR^2$ or —A—$CH(OR^3)$—R, wherein A is an ethylene group, a vinylene group, or an ethynylene group, R is a substituted or unsubstituted $C_{1-10}$ alkyl group, a substituted or unsubstituted $C_{1-10}$ alkenyl group, a substituted or unsubstituted $C_{1-10}$ alkynyl group, a substituted or unsubstituted $C_{3-8}$ cycloalkyl group, a substituted or unsubstituted aralkyl group, or a substituted or unsubstituted aryloxy group, and each of $R^2$ and $R^3$ which are independent of each other is a hydrogen atom or a protecting group for a hydroxyl group.

11. The process according to claim 10, wherein $R^1$ is a protecting group for a hydroxyl group, and $R^5$ is —$CH_2OR^2$ (wherein $R^2$ is a protecting group for a hydroxyl group).

12. The process according to claim 10, wherein $R^1$ is a protecting group for a hydroxyl group, $R^5$ is —A—$CH(OR^3)$—R, wherein R is a $C_{4-10}$ branched alkyl group, a $C_{4-10}$ alkenyl group, a $C_{4-10}$ alkynyl group, or a $C_{1-2}$ alkyl group having a tolyl group, and $R^3$ is a protecting group for a hydroxyl group.

13. The process according to claim 10, wherein the fluorination is carried out by reacting an electrophilic fluorinating agent in the presence of a metal compound under a basic condition.

* * * * *